United States Patent [19]

Henzi

[11] 4,289,693
[45] Sep. 15, 1981

[54] AZO DYES HAVING A QUATERNIZED HETEROCYCLIC DIAZO COMPONENT RADICAL AND AN OPTIONALLY SUBSTITUTED ARYLOXYALKYL SUBSTITUENT ON THE AMINO GROUP OF THE COUPLING COMPONENT RADICAL

[75] Inventor: Beat Henzi, Neuallschwil, Switzerland

[73] Assignee: Sandoz Ltd., Basel, Switzerland

[21] Appl. No.: 746,507

[22] Filed: Dec. 1, 1976

Related U.S. Application Data

[63] Continuation of Ser. No. 383,782, Jul. 30, 1973, abandoned.

[30] Foreign Application Priority Data

Jul. 31, 1972 [CH] Switzerland .................. 11354/72
Dec. 7, 1972 [CH] Switzerland .................. 17824/72
Feb. 5, 1973 [CH] Switzerland .................. 1618/73

[51] Int. Cl.³ .............. C07C 107/04; C09B 44/18; C09B 44/20; C09B 44/10
[52] U.S. Cl. ................... 260/146 R; 260/145 C; 260/146 D; 260/147; 260/154; 260/155; 260/156; 260/157; 260/158; 260/159; 260/160; 260/161; 260/162; 260/163
[58] Field of Search ............ 260/146 R, 146 D, 147, 260/154, 155, 156, 157, 158, 162, 163, 159, 160, 161, 145 C

[56] References Cited

U.S. PATENT DOCUMENTS

| | | | |
|---|---|---|---|
| 3,332,930 | 7/1967 | Mohr et al. ................. | 260/157 X |
| 3,515,715 | 6/1970 | Straley et al. ............... | 260/163 |
| 3,679,656 | 7/1972 | Iizuka et al. ................ | 260/146 R X |
| 3,697,501 | 10/1972 | Dehnert ..................... | 260/163 |
| 3,707,532 | 12/1972 | Artz et al. .................. | 260/158 |
| 3,763,140 | 10/1973 | Entschel et al. ............. | 260/163 X |
| 3,770,716 | 11/1973 | Ozutsumi et al. ............ | 260/146 R |
| 4,051,117 | 9/1977 | Kohlthall et al. ............ | 260/157 |

FOREIGN PATENT DOCUMENTS

| | | | |
|---|---|---|---|
| 657908 | 2/1963 | Canada ...................... | 260/156 |
| 1943800 | 4/1970 | Fed. Rep. of Germany ...... | 260/157 |
| 2059096 | 1/1972 | Fed. Rep. of Germany ...... | 260/158 |
| 1144237 | 10/1957 | France ...................... | 260/158 |
| 1094309 | 12/1967 | United Kingdom ............ | 260/155 |
| 1276686 | 6/1972 | United Kingdom ............ | 260/158 |

*Primary Examiner*—Charles F. Warren
*Attorney, Agent, or Firm*—Gerald D. Sharkin; Richard E. Vila; Melvyn M. Kassenoff

[57] ABSTRACT

Basic dyes free from sulfo groups of the formula

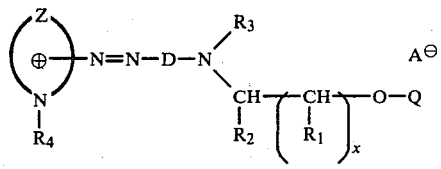

in which Q signifies an unsubstituted or substituted phenyl or naphthyl radical, $R_1$ and $R_2$ signify hydrogen, unsubstituted or substituted alkyl, phenyl or cycloalkyl, $R_3$ signifies hydrogen, unsubstituted or substituted alkyl or phenyl, the Z containing group signifies a heterocyclic diazo radical containing a quaternary ammonium group, $R_4$ signifies unsubstituted or substituted alkyl, alkenyl, cycloalkyl or alkoxy, x signifies 1 to 3, $A^{\ominus}$ signifies an anion, and D signifies an unsubstituted or substituted phenylene or naphthylene radical are useful for dyeing and printing homo- and co-polymers of acrylonitrile and asymmetrical dicyanoethylene and synthetic polyamides and polyesters modified to contain acid groups. The obtained dyeings are level and fast to light and wet treatments.

49 Claims, No Drawings

AZO DYES HAVING A QUATERNIZED HETEROCYCLIC DIAZO COMPONENT RADICAL AND AN OPTIONALLY SUBSTITUTED ARYLOXYALKYL SUBSTITUENT ON THE AMINO GROUP OF THE COUPLING COMPONENT RADICAL

This application is a continuation of application Ser. No. 383,782, filed July 30, 1973 and now abandoned.

The invention relates to basic azo compounds free from sulphonic acid groups.

The invention provides compounds of formula I,

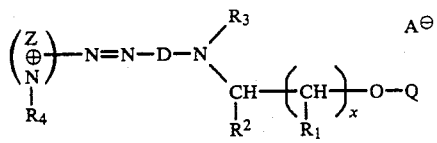

in which
Q signifies a radical of the formula

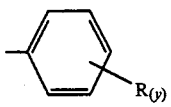

or

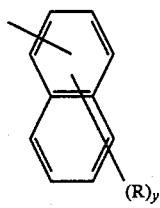

R signifies hydrogen; hydroxy; halogen; alkyl or alkoxy of 1 to 4 carbon atoms, unsubstituted or substituted by halogen, hydroxy, cyano, phenyl or phenoxy; cycloalkyl of 5 or 6 carbon atoms, unsubstituted or substituted by alkyl of 1 to 4 carbon atoms; cyano; nitro; trihalomethyl; trifluoromethyl; phenoxy; naphthyloxy, phenylazo; or a radical of the formula $-CORo$,

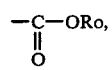

$-SO_2-Ro$, $-SO_2-NH-Ro$,

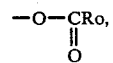

$-O-CO-NH-Ro$, $-O-CO-N(Ro)_2$, $-SO_2-N(Ro)_2$, $-CO-NH-Ro$, $-OSO_2N(Ro)_2$, $-CO-N(Ro)_2$, $-NH-CO-Ro$,

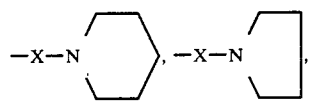

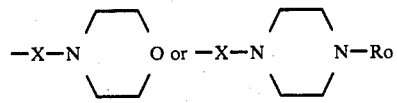

in which the Ro's, independently, signify $C_{1-4}$ alkyl or phenyl, and X signifies $-CO-$ or $-SO_2-$;

$R_1$ and $R_2$, which may be the same or different, signify hydrogen; alkyl of 1 to 4 carbon atoms, unsubstituted or substituted by halogen, $C_{1-4}$ alkoxy or phenoxy; phenyl; or $C_{5-6}$ cycloalkyl;

$R_3$ signifies hydrogen; alkyl of 1 to 12 carbon atoms, unsubstituted or substituted by halogen, hydroxy, cyano, phenyl, phenoxy, $C_{1-4}$ alkoxycarbonyl, $C_{1-4}$ alkylcarbonyloxy, $C_{1-4}$ alkoxy, phenylcarbonyloxy (benzoyloxy),

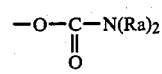

or $-CON(Ra)_2$ in which the Ra's, independently, signify hydrogen or $C_{1-4}$ alkyl; or phenyl;

Z signifies a residue which together with the nitrogen atom forms an unsaturated heterocyclic ring containing at least five ring atoms, which may be carbon, oxygen, sulphur or further nitrogen atoms, which ring optionally has an aromatic carbocyclic or heterocyclic ring fused thereto and is, along with any ring fused thereto, optionally substituted by substituents selected from alkyl of 1 to 4 carbon atoms and alkoxy of 1 to 4 carbon atoms, each unsubstituted or substituted by phenyl, hydroxy, $-CONH_2$, cycloalkyl of 5 or 6 carbon atoms, cyano or halogen; cycloalkyl of 5 or 6 carbon atoms, unsubstituted or substituted by $C_{1-4}$ alkyl, $C_{1-4}$ alkoxy or halogen; phenyl or phenoxy, each unsubstituted or substituted by cyano, nitro, $C_{1-4}$ alkyl, $C_{1-4}$ alkoxy or halogen; halogen; nitro; cyano; trifluoromethyl; a radical of the formula $-CO-Ro$,

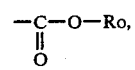

$-NH-SO_2-Ro$, $-CO-NHRo$, $-CO-N(Ro)_2$, $-NH-CO-Ro$, $-SO_2-Ro$, $-SO_2-N(Ro)_2$ or $-SO_2-NHRo$, in which Ro is as defined above; or phenylazo; the

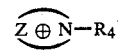

group being free from water-solubilizing groups and containing at least one quaternary nitrogen atom, and being bound to the azo group through a carbon atom, $R_4$ signifies a $C_{1-8}$ alkyl, $C_{2-8}$ alkenyl or $C_{1-4}$ alkoxy radical, each unsubstituted or substituted by halogen, hydroxy, cyano, phenyl, phenoxy, cycloalkyl of 5 or 6 carbon atoms, alkoxy of 1 to 4 carbon atoms or the group $-CONH_2$; or a cycloalkyl radical of 5 or 6 carbon atoms, unsubstituted or substituted by $C_{1-4}$ alkyl; or the group

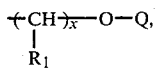

y signifies 1, 2, 3, 4 or 5, and, where y signifies 2 or more, the R's may be the same or different, x signifies 1, 2 or 3, $A^{\ominus}$ signifies an organic or inorganic anion, and D signifies a phenylene or naphthylene radical, each further unsubstituted or further substituted by 1 or 2 substituents selected from $C_{1-4}$ alkoxy, $C_{1-4}$ alkyl and halogen.

Any heterocyclic ring in

is preferably of 5 or 6 ring atoms and preferably contains 1, 2 or 3 heteroatoms.

As examples of radicals

may be given thiazolyl, isothiazolyl, thiadiazolyl, triazolyl, imidazolyl, indazolyl, oxazolyl, pyridinyl, pyrimidinyl, pyridazinyl, pyrazinyl, benzothiazolyl, oxadiazolyl, quinoxalinyl, cinnolinyl, quinolinyl, phthalazinyl, pyrazolyl, benzoxazolyl and benzimidazolyl derivatives.

Preferred examples of

are the triazolyl, pyridinyl, benzothiazolyl, quinolinyl and indazolyl derivatives, more preferably the triazolyl, pyridinyl and benzothiazolyl derivatives and most preferably the triazolyl derivatives.

In the compounds of formula I, where Q signifies a naphthalene radical, such radical is preferably unsubstituted.

The preferred compounds of Formula I are those wherein $R_1$ is hydrogen, $C_{1-4}$alkyl or phenyl, $R_2$ is hydrogen, $R_3$ is hydrogen; $C_{1-4}$alkyl or $C_{1-4}$alkyl substituted by phenoxy, phenyl, $C_{1-4}$alkoxycarbonyl or benzoyloxy, $R_4$ is $C_{1-4}$alkyl; $C_{1-4}$alkyl substituted by phenyl, hydroxy or $-CONH_2$; or $C_{1-4}$alkoxy,

is a triazolyl, pyridyl, benzothiazolyl, quinolyl or indazolyl derivative, preferably a triazolyl, pyridyl or benzothiazolyl derivative, most preferably a triazolyl derivative, D is phenylene, naphthylene or phenylene substituted in a position ortho to the azo radical by $C_{1-4}$alkyl, $C_{1-4}$alkoxy or halo, and Q is phenyl, naphthyl, phenyl substituted by 1 or 2 R's or phenyl substituted by 3, 4 or 5 halo substituents.

As examples of anions $A^{\ominus}$ may be given the halides, such as chloride, bromide or iodide, sulphate, bisulfate, methylsulphate, aminosulphate, perchlorate, carbonate, bicarbonate, phosphate, phosphormolybdate, phosphortungstenate, phosphortungstenmolybdate, formate, benzenesulphonate, naphthalenesulphonate, 4-chlorobenzenesulphonate, oxalate, maleinate, acetate, propionate, lactate, succinate, chloroacetate, tartrate, malate, methanesulphonate or benzoate ions, or complex anions such as zinc chloride double salts, e.g. $ZnCl_3^{\ominus}$. The preferred anions are the halide preferably chloride, methylsulphate $ZnCl_3^{\ominus}$ and acetate ions.

Even more preferred are the compounds of Formula I wherein $R_1$ is hydrogen, methyl or phenyl, $R_2$ is hydrogen, $R_3$ is methyl, ethyl, butyl, phenoxyethyl, benzyl, ethoxycarbonylethyl or benzoyloxyethyl, $R_4$ is methyl, ethyl, benzyl, 2-hydroxyethyl, 2-hydroxypropyl, 2-carbamoylethyl or methoxy,

is a triazolyl, pyridyl or benzothiazolyl derivative, especially a triazolyl derivative, D is phenylene, naphthylene or phenylene substituted in a position ortho to the azo radical by methyl, methoxy or chloro, Q is phenyl, naphthyl, phenyl substituted by 3, 4 or 5 chloro substituents or phenyl substituted by 1 or 2 substituents selected from chloro, $C_{1-4}$alkyl, benzyl, nitro, cyano, phenylsulfonyl, methylsulfamoyl, dimethylsulfamoyl, trifluoromethyl, methoxycarbonyl, methylcarbamoyl, methoxy, phenoxy, benzoyloxy, phenylazo, benzamido, phenylcarbamoyloxy, dimethylcarbamoyloxy, N-methyl-N-phenylcarbamoyloxy, methylsulfonyl, dimethylsulfamoyloxy, phenoxymethyl, benzoyl or hydroxy (especially phenyl, naphthyl, phenyl substituted by 2, 3, 4 or 5 chloro substituents, phenyl monosubstituted by one of the aforementioned substituents or phenyl substituted by hydroxy and by benzoyl), and x is 1 or 2.

Thus, the preferred compounds of Formula I' when P is a group of Formula (a), or an isomer thereof of formula (b) or (c), are those wherein $R_8$ is $C_{1-4}$alkyl or $C_{1-4}$alkyl substituted by phenyl, hydroxy or carbamoyl, $R_9$ is $C_{1-4}$alkyl or $C_{1-4}$alkyl substituted by phenyl, hydroxy or carbamoyl, and $R_{10}$ is hydrogen, $C_{1-4}$alkyl or $C_{1-4}$alkyl substituted by phenyl, especially those of the group wherein $R'_1$ is hydrogen or $C_{1-4}$alkyl, $R'_2$ is hydrogen, $R'_3$ is $C_{1-4}$alkyl or $C_{1-4}$alkyl substituted by phenoxy, $R'_7$ is hydrogen, $C_{1-4}$alkyl or $C_{1-4}$alkoxy, B is 1,4-phenylene, Q' is phenyl, naphthyl, phenyl substituted by 3, 4 or 5 chloro substituents or phenyl substituted by 1 or 2 substituents selected from halo, nitro, cyano, phenylsulfonyl, $C_{1-4}$alkylsulfamoyl, di-($C_{1-4}$alkyl)-sulfamoyl, ($C_{1-4}$alkoxy)carbonyl, ($C_{1-4}$alkyl)carbamoyl, $C_{1-4}$alkoxy, benzoyl, phenoxy, benzoyloxy, phenylazo, benzamido, phenylcarbamoyloxy, di-($C_{1-4}$alkyl)carbamoyloxy, N-$C_{1-4}$alkyl-N-phenylcarbamoyloxy, $C_{1-4}$alkylsulfonyl, di-($C_{1-4}$alkyl)sulfamoyloxy, trifluoromethyl, $C_{1-4}$alkyl or phenyl($C_{1-4}$alkyl), and x is 1, and particularly those of the immediately preceding group wherein $A^\ominus$ is chloride, $ZnCl_3^\ominus$, methylsulfate or acetate or wherein $R_8$ is methyl,
$R_9$ is methyl, and
$R_{10}$ is hydrogen.

Even more preferred compounds of Formula I' when P is a group of Formula (a), or an isomer thereof of Formula (b) or (c), are those wherein $R'_1$ is hydrogen or $C_{1-4}$alkyl,
$R'_2$ is hydrogen,
$R'_3$ is methyl or ethyl,
$R'_7$ is hydrogen
$R_8$ is methyl,
$R_9$ is methyl,
$R_{10}$ is hydrogen,
B is 1,4-phenylene,
Q' is phenyl, 2-naphthyl, phenyl substituted by 1 to 5 chloro substituents or phenyl monosubstituted by nitro, cyano, phenylsulfonyl, methylsulfamoyl, dimethylsulfamoyl, methoxycarbonyl, methylcarbamoyl, methoxy, phenoxy, benzoyloxy, phenylazo, benzamido, phenylcarbamoyloxy, dimethylcarbamoyloxy, N-methyl-N-phenylcarbamoyloxy, methylsulfonyl, dimethylsulfamoyloxy, trifluoromethyl, methyl or benzyl (especially those wherein when Q' is monosubstituted phenyl, the substituent is in the para position), and x is 1, especially those of this group wherein $A^\ominus$ is chloride, $ZnCl_3^\ominus$, methylsulfate or acetate.

The invention also provides a process for the production of compounds of formula I, characterised by quaternising a compound of formula II,

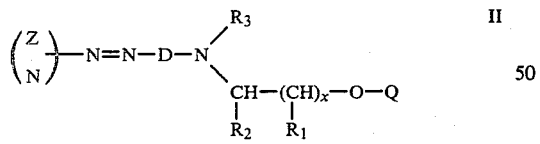

in which Z, D, $R_1$, $R_2$, $R_3$ x and Q are as defined above, by reaction with a compound of formula III, $$R_4—A \qquad \text{III}$$

in which $R_4$ is as defined above, and A corresponds to $A^\ominus$, above, or by addition reaction of an $R_4$ yielding epoxide or vinyl compound with a compound of formula II, in the presence of water and with neutralization employing an acid HA.

The quaternisation with a compound of formula III may be carried out in conventional manner. Suitably, the reaction is carried out in an inert solvent, in an aqueous suspension or, where liquid under the reaction conditions, in an excess of the compound of formula III. Where necessary, the reaction can be carried out at elevated temperatures and in a buffered medium. As examples of preferred quaternising agents of formula III may be given methyl or ethyl chloride, bromide or iodide, alkyl sulphates, such as dimethyl sulphate, or benzyl chloride. As examples of other quaternising agents may be given acrylic acid amide hydrochloride, such as $CH_2=CH—CO—NH_2/HCl$, chloroacetic acid amide, or epoxides such as ethylene oxide and propylene oxide, and epichlorohydrins, in the presence of an acid of the formula HA.

Preferred compounds of formula I are compounds of formula I',

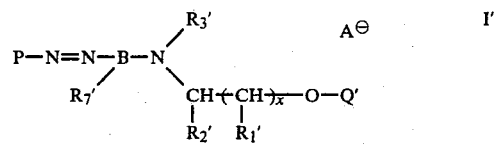

in which P signifies a radical of the formula

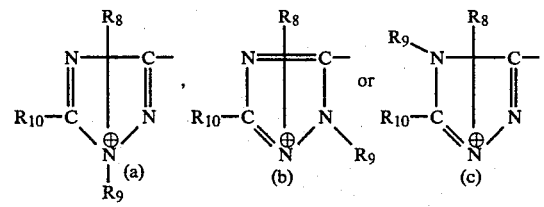

in which $R_8$ signifies an alkyl radical of 1 to 4 carbon atoms or alkenyl radical of 2 to 4 carbon atoms, unsubstituted or substituted by hydroxy, halogen, cyano, phenyl or the group —$CONH_2$; or a cyclohexyl radical, unsubstituted or substituted by $C_{1-4}$alkyl, $R_9$ signifies an alkyl radical of 1 to 4 carbon atoms, unsubstituted or substituted by hydroxy, halogen, cyano, phenyl or the group —$CONH_2$; a cyclohexyl radical, unsubstituted or substituted by $C_{1-4}$alkyl; or a phenyl radical, unsubstituted or substituted by halogen, $C_{1-4}$alkyl or $C_{1-4}$alkoxy, $R_{10}$ signifies hydrogen or one of the significances of $R_9$, above, a radical of the formula

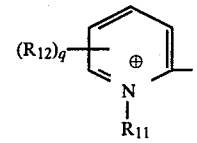

in which $R_{11}$ signifies $C_{1-4}$alkoxy, $C_{1-4}$alkyl or $C_{2-4}$alkenyl, each unsubstituted or substituted by hydroxy, halogen, cyano, phenyl or the group —$CONH_2$, $R_{12}$ signifies phenyl; halogen; nitro; cyano; $C_{1-4}$alkyl or $C_{1-4}$alkoxy;

q signifies 0, 1 or 2; and where q signifies 2, the $R_{12}$'s may be the same or different, a radical of the formula

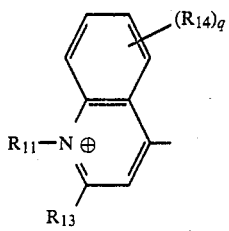

in which $R_{13}$ signifies a $C_{1-4}$alkyl radical,
$R_{14}$ signifies halogen, nitro, cyano, trifluoromethyl, $C_{1-4}$alkylsulphonyl or, di-$(C_{1-14}$alkyl)sulfamoyl or phenylsulphonyl,
$R_{11}$ is as defined above, and
q is a defined above, and when q signifies 2, the $R_{14}$'s may be the same or different;
a radical of the formula

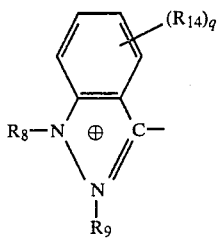

(f)

in which $R_8$, $R_9$, $R_{14}$ and q are as defined above; and when q signifies 2, the $R_{14}$'s may be the same or different;
or a radical of the formula

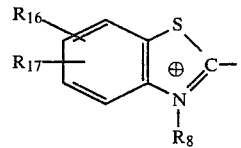

(g)

in which $R_8$ is as defined above,
either $R_{16}$ and $R_{17}$, which may be the same or different, each signifies hydrogen; halogen; $C_{1-4}$alkyl or $C_{1-4}$alkoxy, unsubstituted or substituted by phenyl, hydroxy, —$CONH_2$, cycloalkyl of 5 or 6 carbon atoms, cyano or halogen; phenoxy; or a radical of the formula —CO—Ro,

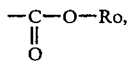

—NH—$SO_2$—Ro, —CO—NH—Ro, —CON(Ro)$_2$, —NH—CO—Ro, —$SO_2$—Ro, —$SO_2$—NH—Ro or —$SO_2$—N(Ro)$_2$; in which Ro is as defined above,
or $R_{16}$ and $R_{17}$ are on adjacent carbon atoms and are linked to form a —CH=CH—CH=CH— linkage;
$R'_3$ signifies hydrogen; or a $C_{1-4}$alkyl radical, unsubstituted or substituted by phenyl, halogen, $C_{1-4}$alkoxy, phenoxy, $C_{1-4}$alkylcarbonyloxy, phenylcarbonyloxy, cyano or N,N-di($C_{1-4}$)alkylcarbamoyl,
either B signifies a 1,4-phenylene radical, and $R'_7$ is in a position of said radical ortho to the —N=N— group and signifies hydrogen; halogen; $C_{1-4}$alkyl or $C_{1-4}$alkoxy,
or B signifies a naphthylene radical, preferably a 1,4-naphthylene radical, and
$R'_7$ signifies hydrogen;
$R'_1$ and $R'_2$ which may be the same or different, each signifies hydrogen, phenyl, or $C_{1-4}$alkyl,
Q'' signifies an unsubstituted naphthyl radical, an unsubstituted phenyl radical, or a phenyl radical substituted by up to 5 halogen atoms or up to two substituents selecting from nitro; halogen; hydroxy; cyano; trihalomethyl; trifluoromethyl; alkyl or alkoxy of 1 to 4 carbon atoms, unsubstituted or substituted by phenyl or phenoxy; phenylazo; cyclohexyl; benzoyloxy; phenylcarbamoyloxy; a group —CORo,

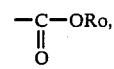

—$SO_2$—Ro, —$SO_2$—NH—Ro, —$SO_2$—N(Ro)$_2$, —CO—NH—Ro, —CO—N(Ro)$_2$, O—CO—N(Ro)$_2$ or —NH—CO—Ro, in which Ro is as defined above;

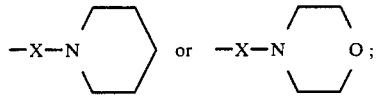

in which X is as defined above,
x signifies 1, 2 or 3, preferably 1;
$A^\ominus$ is as defined above, preferably a halide $ZnCl_3^\ominus$ methylsulfate ion or acetate ion.
As will be appreciated, formulae (b) and (c), above, are isomeric forms of formula (a). For convenience, only one formula will be given hereinafter, it being understood to embrace the isomers. Mixtures of the isomers are obtained when producing the compounds.
In the compounds of formula I', P preferably signifies a radical (a) or an isomer (b) or (c) thereof, a radical (d) or a radical (g). Most preferably P signifies a radical (a) or an isomer (b) or (c) thereof.
In radical (a), or isomer (b) or (c) thereof, $R_8$ preferably signifies an alkyl radical of 1 to 4, more preferably 1 or 2, carbon atoms, unsubstituted or substituted by phenyl, e.g. a benzyl radical, hydroxy, e.g. 2-hydroxyethyl and 2-hydroxypropyl, or the group —$CONH_2$, e.g. 2-carboxyamidoethyl (2-carbamoylethyl). $R_8$ most preferably signifies a methyl radical. $R_9$ preferably signifies an unsubstituted $C_{1-4}$, more preferably $C_{1-2}$, alkyl radical, or a $C_{1-4}$, more preferably $C_{1-2}$, alkyl radical substituted by phenyl, e.g. benzyl and phenylethyl, hydroxy, e.g. 2-hydroxyethyl and 2-hydroxypropyl, or the group —$CONH_2$, e.g. 2-carbamoylethyl. Most preferably $R_9$ signifies a methyl radical. $R_{10}$ preferably signifies a hydrogen atom, a phenyl radical, a cyclohexyl radical, an unsubstituted $C_{1-4}$, more preferably $C_{1-2}$, alkyl radical, or a $C_{1-4}$ alkyl, more preferably $C_{1-2}$, alkyl radical substituted by phenyl, e.g. a benzyl radical. $R_{10}$ most preferably signifies a hydrogen atom.
Where P signifies a radical (a), or an isomer (b) or (c) thereof, $R'_3$ preferably signifies an alkyl radical of 1 to 4 carbon atoms, unsubstituted or substituted by phenoxy, e.g. 2-phenoxyethyl, phenyl, e.g. benzyl, $C_{1-4}$alkoxycarbonyl, e.g. 2-ethoxy carbonylethyl, or phenylcarbonyloxy, e.g. 2-phenylcarbonyloxyethyl. R'₃ more preferably signifies an unsubstituted C₁₋₄alkyl, particularly a methyl or ethyl, radical. Most preferably, R'₃ signifies an ethyl radical. R'₂ preferably signifies a hydrogen atom. R'₁ preferably signifies a hydrogen atom, or a C₁₋₄alkyl radical, e.g. a methyl radical. R'₁ most preferably signifies a hydrogen atom or a methyl radical, particularly a hydrogen atom. B preferably signifies a phenylene radical. R'₇ preferably signifies a hydrogen atom, a C₁₋₄alkyl radical or a C₁₋₄alkoxy radical. More preferably R₇ signifies a hydrogen atom or a methyl radical and, most preferably, signifies a hydrogen atom. Q' preferably signifies an unsubstituted naphthyl radical, preferably a 2-naphthyl radical, an unsubstituted phenyl radical or a phenyl radical substituted by up to 5 halogen atoms, preferably chlorine atoms, or by up to two substituents, which may be the same or different, selected from halogen, e.g. chlorine, nitro, cyano, phenylsulfonyl, —SO₂NH(C₁₋₄alk), preferably —SO₂NHCH₃, —SO₂N(C₁₋₄alk)₂, preferably —SO₂N(CH₃)₂,

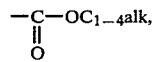

preferably

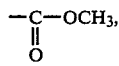

O—Co—N(C₁₋₄alkyl)₂, preferably

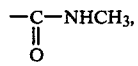

C₁₋₄alkoxy, preferably methoxy, phenoxy, phenylcarbonyloxy, phenylazo, phenylcarbonylamino, phenylaminocarbonyloxy,

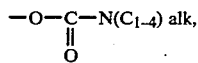

preferably N,N-dimethylaminocarbonyloxy, N(C₁₋₄alk)-N-phenylaminocarbonyloxy, preferably N-methyl-N-phenylaminocarbonyloxy, C₁₋₄alkylsulphonyl, preferably methylsulphonyl, di-(C₁₋₄)alkylaminosulphonyloxy, preferably dimethylaminosulphonyloxy, trifluoromethyl, unsubstituted C₁₋₄alkyl, preferably methyl, or C₁₋₄alkyl substituted by phenyl, preferably benzyl. Where Q signifies a phenyl radical substituted by up to two such substituents it is generally only monosubstituted. Where Q is monosubstituted, the substituent is preferably in the para-position. The most preferred significances of Q' are 2-naphthyl, unsubstituted phenyl and phenyl substituted by up to 5 halogen atoms, preferably chlorine atoms. A⊖ preferably signifies a Cl⊖, ZnCl₃⊖, CH₃SO₄⊖, or acetate ion. x preferably signifies 1.

Where P signifies a radical of formula (d), R₁₁ preferably signifies an alkyl radical of 1 to 4, preferably 1 or 2, carbon atoms or an alkoxy radical of 1 to 4 carbon atoms, preferably a methoxy radical. R₁₁ most preferably signifies a methyl radical. R₁₂ preferably signifies hydrogen, a C₁₋₄alkyl radical, preferably a methyl radical, C₁₋₄alkoxy radical, preferably a methoxy radical, or a halogen atom, preferably chlorine. R₁₂ most preferably signifies hydrogen. q preferably signifies 1. R'₃ preferably has a significance as given above, when P signifies (a), more preferably an alkyl radical or 1 to 4 carbon atoms, most preferably a methyl or ethyl radical. R'₂ preferably signifies a hydrogen atom. R'₁ preferably has a significance as given above, when P signifies (a), more preferably methyl or hydrogen, and most preferably a hydrogen atom. B preferably signifies a phenylene radical. R'₇ preferably has a significance as given above, when P signifies (a), more preferably a hydrogen atom or an alkyl radical of 1 to 4 carbon atoms, e.g. methyl, most preferably hydrogen. Q' preferably has a significance as given above, where P signifies (a), more preferably an unsubstituted 2-naphthyl or phenyl radical, or a phenyl radical substituted by up to 5 halogen, preferably chlorine, atoms. A⊖ preferably signifies Cl⊖, ZnCl₃⊖, CH₃⊖SO₄ or an acetate ion, and x preferably signifies 1.

Where P signifies a radical of formula (g), R₈ preferably signifies an alkyl radical of 1 to 4, preferably 1 or 2, carbon atoms, unsubstituted or substituted by -CONH₂, e.g. 2-carbamoylethyl. R₈ more preferably signifies a methyl or ethyl radical, most preferably a methyl radical. R₁₆ and R₁₇, which may be the same or different, each preferably signify hydrogen; chlorine, C₁₋₄ alkoxy, preferably methoxy, unsubstituted or substituted by phenyl, e.g. benzyloxy; C₁₋₄ alkylcarbonyl, preferably methylcarbonyl; C₁₋₄ alkylaminocarbonyl, preferably methylaminocarbonyl; phenylcarbonylamino; C₁₋₄ alkylsulphonylamino, preferably methylsulphonylamino; phenoxy; di-C₁₋₄ (di-C₁₋₄alkylsulfamoyl), preferably dimethylaminosulphonyl; or phenylsulphonyl, or R₁₆ and R₁₇ are on adjacent carbon atoms and form a —CH=CH—CH=CH— linkage. Most preferably one of R₁₆ and R₁₇ signifies hydrogen, the other methoxy. R₃' preferably has one of the significances given above, when P signifies (a), more preferably a methyl or ethyl radical. R₂' preferably signifies a hydrogen atom. R₁' preferably has a significance given above when P signifies (a), more preferably methyl or hydrogen. B preferably signifies a phenylene radical. R₇ preferably has a significance given above, when P signifies (a), more preferably methyl or hydrogen, most preferably hydrogen. Q' preferably has a significance given above, where P signifies (a), most preferably an unsubstituted 2-naphthyl radical, an unsubstituted phenyl radical or a phenyl radical substituted by up to 5 halogen, preferably chlorine, atoms. X preferably signifies 1 and A⊖ preferably signifies Cl⊖, ZnCl₃⊖, CH₃SO₄⊖ or an acetate ion.

Thus, the preferred compounds of Formula I' when P is a group of Formula (g) are those where
R₈ is C₁₋₄alkyl or C₁₋₄alkyl substituted by carbamoyl, and
each of R₁₆ and R₁₇ is independently hydrogen; C₁₋₄alkoxy; C₁₋₄alkoxy substituted by phenyl; C₁₋₄alkylcarbonyl; C₁₋₄alkylcarbamoyl; benzamido; C₁₋₄alkylsulfonylamino; phenoxy or phenylsulfonyl or
R₁₆ and R₁₇ taken together are —CH=CH—CH=CH—,
especially those of this group wherein
R₁' is hydrogen or methyl,
R₂' is hydrogen,
R₃' is methyl or ethyl,
R₇' is hydrogen or methyl, B is 1,4-phenylene, Q is phenyl, naphthyl or phenyl substituted by 1 to 5 chloro substituents, and x is 1.

Representative compounds of formula I' are those in which x signifies 1, $R_2'$ signifies hydrogen, $R_1'$ signifies a hydrogen atom or an alkyl radical of 1 to 4 carbon atoms, and P signifies a radical of the formula

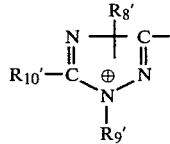
(a')

in which $R_8'$ and $R_9'$, which may be the same or different, each signifies an alkyl radical of 1 to 4 carbon atoms, unsubstituted or substituted by phenyl, hydroxy or —$CONH_2$;

$R_{10}'$ signifies a hydrogen atom, an alkyl radical of 1 to 4 carbon atoms, a phenyl ($C_{1-4}$)alkyl radical or a phenyl radical;

a radical of the formula

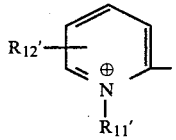
(b')

in which $R_{11}'$ signifies $C_{1-4}$ alkyl;

$R_{12}'$ signifies hydrogen; halogen; $C_{1-4}$ alkyl or $C_{1-4}$ alkoxy;

a radical of the formula

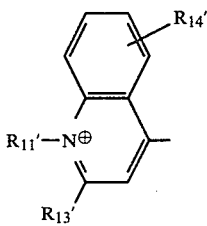
(e')

in which $R_{13}'$ signifies hydrogen or an alkyl radical of 1 to 4 carbon atoms, $R_1'$ is as defined above, and $R_{14}'$ signifies hydrogen;

a radical of the formula

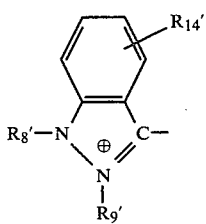
(f')

in which $R_8'$, $R_{14}'$ and $R_9'$ are as defined above, or a radical of the formula

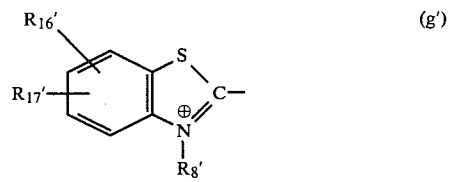
(g')

in which either $R_{16}'$ and $R_{17}'$, which may be the same or different, each signifies hydrogen; $C_{1-4}$ alkyl or $C_{1-4}$ alkoxy, unsubstituted or substituted by phenyl or phenoxy;

or $R_{16}'$ and $R_{17}'$ are on adjacent carbon atoms and are linked to form a —CH=CH—CH=CH— linkage; and $R_8'$ is as defined above.

Still further preferred compounds of formula I are the compounds of the formula I",

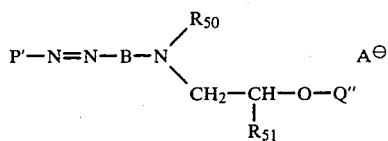
I"

in which P' signifies a radical of formula

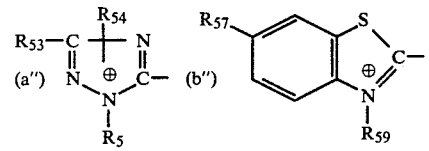

or an isomer thereof,

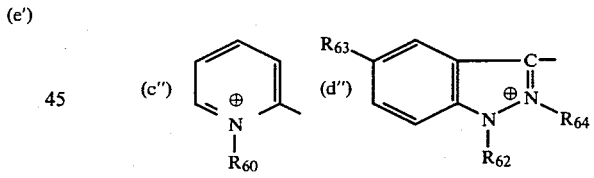

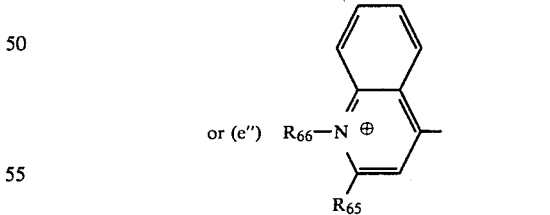

in which $R_{53}$ signifies a hydrogen atom, a methyl radical, a phenyl radical or a benzyl radical.

$R_{54}$ and $R_{55}$, independently, signify an unsubstituted alkyl radical of 1 to 4 carbon atoms, preferably a methyl or ethyl radical, or an alkyl radical of 1 to 4 carbon atoms substituted by a hydroxy radical or the group —$CONH_2$, $R_{57}$ signifies a hydrogen atom or an alkoxy radical of 1 to 4 carbon atoms, preferably a methoxy radical, $R_{59}$ signifies an alkyl radical of 1 to 4 carbon atoms, preferably a methyl or ethyl radical, unsubstituted or substituted by the group —$CONH_2$, $R_{60}$ signifies an alkyl or alkoxy radical of 1 to 4 carbon atoms, preferably a methyl or ethyl radical, $R_{62}$ signifies an alkyl radical of 1 to 4 carbon atoms, preferably a methyl radical, $R_{63}$ signifies a hydrogen atom or a group $(C_{1-4}alk)_2NSO_2$—, preferably $(CH_3)_2NSO_2$—, $R_{64}$ signifies an alkyl radical of 1 to 4 carbon atoms, preferably a methyl radical, $R_{65}$ and $R_{66}$, which may be the same or different, each signify an alkyl radical of 1 to 4 carbon atoms, preferably a methyl radical, B signifies a 1,4-phenylene radical, unsubstituted or substituted in the ortho position to the azo group by alkyl of 1 to 4 carbon atoms, preferably methyl, $R_{50}$ signifies an alkyl radical of 1 to 4 carbon atoms, unsubstituted or substituted by phenyl, $R_{51}$ signifies a hydrogen atom or an alkyl radical of 1 to 4 carbon atoms, preferably a methyl radical, Q" signifies an unsubstituted naphthyl, preferably a 2-naphthyl, radical, an unsubstituted phenyl radical, a phenyl radical substituted by up to two substituents, preferably one substituent, selected from hydroxy, halogen, preferably chlorine, $C_{1-4}$ alkoxycarbonyl, preferably methoxycarbonyl, phenoxy, phenylcarbonyl, cyclohexyl, alkyl of 1 to 4 carbon atoms, preferably methyl, unsubstituted or substituted by up to three halogen atoms or by a phenyl radical; or Q" signifies a phenyl radical substituted by up to 5 halogen atoms, preferably chlorine atoms, and $A^\ominus$ is as defined above, preferably chloride, $ZnCl_3^\ominus$, methylsulfate or acetate.

In the compounds of formula I", P' preferably signifies a radical of formula (a"), (b") or (c"), most preferably a radical of (a").

Representative of the compounds of formula I" are the compounds of formula Ia",

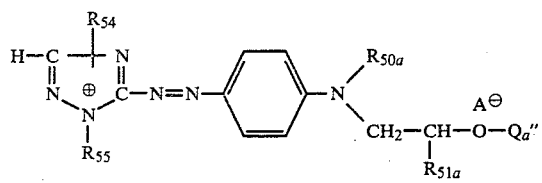

in which $R_{54}$ and $R_{55}$ are as defined above, $R_{50a}$ signifies an unsubstituted alkyl radical of 1 to 4 carbon atoms, preferably a methyl, ethyl or butyl radical;

$R_{51a}$ signifies hydrogen or a methyl radical, $Q_a$" signifies an unsubstituted naphthyl radical, an unsubstituted phenyl radical, a phenyl radical substituted by up to two methyl radicals, a phenyl radical substituted by up to five halogen atoms, preferably chlorine atoms; or a 3-hydroxy-4-phenylcarbonylphenyl radical, and $A^\ominus$ is as defined above, preferably a $ZnCl_3^\ominus$, $Cl^\ominus$, $CH_3SO_4^\ominus$ or acetate ion.

As examples of alkyl and alkoxy radicals of 1 to 4 carbon atoms may be given methyl, ethyl, n-propyl, isopropyl and n-butyl and the corresponding alkoxy radicals. Unless otherwise stated, the preferred such radicals are methyl, ethyl, methoxy and ethoxy, methyl and methoxy being most preferred. By the term halogen, as used herein, is meant chlorine, bromine and iodine; chlorine and bromine being preferred, chlorine being most preferred.

The compounds of formula I are useful as dyes. They may be converted into dyeing preparations, e.g. into stable, liquid or solid dyeing preparations, in conventional manner, e.g. by grinding or granulating or dissolving in conventional dyestuff solvents, if necessary with the addition of assistants such as stabilizers. Such preparations may be produced, for example, in accordance with French Pat. Nos. 1,572,030 and 1,581,900.

The compounds of formula I may be used in the dyeing and printing of textile substrates, whether in fibre, yarn or fibric form, which consist of or comprise homopolymers or co-polymers of acrylonitrile or asymmetrical dicyanoethylene. The dyeing of such substrates may be carried out in conventional manner.

The compounds of formula I may also be used for dyeing or printing substrates of synthetic polyamide or synthetic polyester fibres, modified by the introduction of acid groups. Polyamides of this type are described in Belgian Pat. No. 706,104 and polyester fibres of this type are described in U.S. Pat. No. 3,379,723. The dyeing of such substrates may be carried out in conventional manner. It is advantageous to dye in an aqueous, neutral or acid medium, at from 60° C. to the boil or at temperatures above 100° C. under pressure.

The dyeings obtained with the compounds of formula I are level, have stable light fastness as well as good wet fastness properties, e.g. to washing, perspiration, sublimation, pleating, decatizing, pressing, steam, water, sea water, dry cleaning, crossdyeing and solvents. The dyes are well soluble in water, show good compatibility with salt, good stability to boiling, good pH stability and partly reserve fibres other than those on which they are dyeable. Further, they possess good power of build-up in combination with other basic dyes.

The compounds, which have good solubility in organic solvents, may also be used for the dyeing of natural or synthetic resins in the mass, being incorporated therein in conventional manner, e.g. by intimate admixture therein, for example by milling, optionally with the use of a solvent.

It has been found that mixtures of two or more of the compounds of the present invention or of one of the compounds of the present invention amd other cationic dyes can be used with advantage.

The following Examples, in which parts and percentages are by weight and temperatures are in degrees centigrade, illustrate the invention.

EXAMPLE 1

8.4 Parts of 3-amino-1,2,4-triazole are dissolved in 22 parts of 62% nitric acid and 18 parts water. The solution is mixed with 20 parts ice and over a period of 20 minutes, 20.8 parts 4 N sodium nitrite solution is added dropwise. After 30 minutes the excess nitrite is decomposed with 0.4 parts aminosulphonic acid and the diazo solution is, over a period of 20 minutes, dropped into a solution consisting of 24.1 parts N-ethyl-N-2'-phenoxyethylaniline (prepared according to known methods), 25 parts glacial acetic acid and 10 parts ice. The pH is adjusted to 3.5–4.0 by the addition of a concentrated caustic soda solution, the dyestuff suspension is stirred and filtered to obtain the dye product. The vacuum dried dye is suspended in 150 parts benzene and 35 parts cyclohexane, filtered and washed with 100 parts cyclohexane.

26.8 Parts of the dried and finely ground dye is suspended in 80 parts water, 3.5 parts magnesium oxide and 18 parts dimethylsulphate and heated to 45° to 50° for 30 minutes. After cooling to room temperature, the solution is diluted with 800 parts water, mixed with 2.5 parts "Norit Supra" and filtered using a talc filter. The dye is salted out from the filtrate with 10.2 parts zinc chloride and 80 parts sodium chloride, washed with 100 parts of a 10% aqueous solution of sodium chloride and dried at 50° under vacuum.

34.8 Parts of the dye of the formula

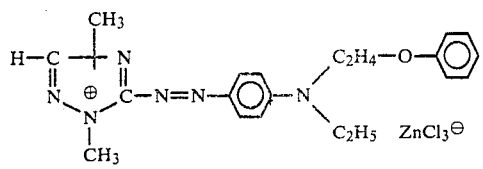

are obtained which on polyacrylonitrile and acid-modified polyester fibres gives bluish-red dyeings.

Application Example A

20 Parts of the dye of Example 1 and 80 parts dextrin are ground for 4 hours in a powder mill. 1 Part of the preparation so obtained is made into a paste with 1 part 40% acetic acid, then 200 parts demineralized water are poured onto the paste and the mixture is boiled for a short time. (The same dye and dextrin mixture can also be formed into a paste with 100 parts water and finally be spray dried.) The mixture is then diluted with 7000 parts demineralized water, mixed with 2 parts glacial acetic acid and is put into a bath at 60° with 100 parts polyacrylonitrile fabric. The fabric may be pretreated for 10 to 15 minutes at 60° in a bath consisting of 8000 parts water and 2 parts glacial acetic acid.

The dyebath is raised to 98° to 100° over a period of 30 minutes, boiled for 1½ hours and the fabric is rinsed. A bluish-red dyeing with good light and wet fastness properties is obtained.

10 Parts of the dye of Example 1 are dissolved in 60 parts glacial acetic acid and 30 parts water. A stable concentrated solution, with a dye content of about 10%, is obtained, which solution can be used to dye polyacrylonitrile according to the above-mentioned process.

Application Example B

20 Parts of the dye of Example 1 are mixed with 80 parts dextrin in a ball-mill for 48 hours; 1 part of the preparation so obtained is made into a paste with 1 part 40% acetic acid; 200 parts demineralized water are poured onto the paste and the mixture is boiled for a short time. With this solution the following dyeings are made:

(a) The solution is diluted with 7000 parts of demineralized water and mixed with 21 parts of anhydrous sodium sulphate, 14 parts of ammonium sulphate, 14 parts of formic acid and 15 parts of a carrier based on the reaction product of ethylene oxide with dichlorophenolene are put into a bath at 60° with 100 parts of a polyester fabric, which fabric has been modified with acid groups. The fabric may be pretreated for 10 to 15 minutes at 60° in a bath consisting of 8000 parts of water and 2 parts of glacial acetic acid.

The dyebath is raised to 98°–100° over a period of 30 minutes, boiled for 1½ hours and the fabric rinsed. A similar bluish-red dyeing with good wet fastness is obtained.

(b) The solution is diluted with 3000 parts of demineralized water and mixed with 18 parts of anhydrous sodium sulphate, together with 6 parts of ammonium sulphate and formic acid and put into the bath at 60° with 100 parts of a polyester fabric, which fabric has been modified with acid groups. The closed vessel is heated to 110° over a period of 45 minutes, kept at this temperature for one hour with shaking, cooled to 60° within 25 minutes and the dyed fabric rinsed. A similar bluish-red dyeing with good wet fastness is obtained.

(c) The same procedure as described in paragraph (b) above is carried out except that the closed vessel is heated for one hour at 120°.

The structural composition of further dyes is shown in the following Table I, which dyes can be produced in accordance with the procedure of Example 1 and agree with the formula

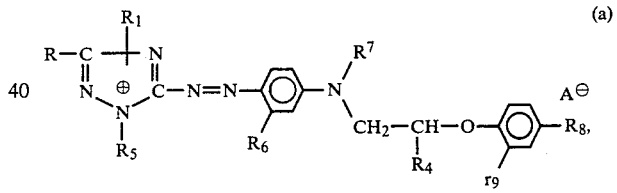

in which R, $R_1$ and $R_4$ to $R_9$ have the significances as shown in the columns of Table I.

The anion $A^\ominus$ may be any one of those named in the foregoing description. A further column indicates the shade of dyeing on polyacrylonitrile.

TABLE I

| Ex. | R | $R_1$ | $R_4$ | $R_5$ | $R_6$ | $R_7$ | $R_8$ | $R_9$ | Dye-shade on polyacrylonitrile |
|---|---|---|---|---|---|---|---|---|---|
| 2 | H | —CH$_3$ | H | —CH$_3$ | H | —C$_2$H$_5$ | H | Cl | bluish-red |
| 3 | H | —CH$_3$ | H | —CH$_3$ | H | —C$_2$H$_5$ | Cl | Cl | " |
| 4 | H | —CH$_3$ | H | —CH$_3$ | H | —C$_2$H$_5$ | —CH$_3$ | H | " |
| 5 | H | —CH$_3$ | H | —CH$_3$ | —CH$_3$ | —C$_2$H$_5$ | H | H | " |
| 6 | H | —CH$_3$ | H | —CH$_3$ | —CH$_3$ | —C$_2$H$_5$ | Cl | H | " |
| 7 | H | —CH$_3$ | H | —CH$_3$ | —CH$_3$ | —C$_2$H$_5$ | —CH$_3$ | H | " |
| 8 | H | —CH$_3$ | H | —CH$_3$ | —OCH$_3$ | —C$_2$H$_5$ | H | H | " |
| 9 | H | —CH$_3$ | H | —CH$_3$ | H | —CH$_3$ | H | H | " |
| 10 | H | —CH$_3$ | H | —CH$_3$ | H | —C$_2$H$_4$—O—⌬ | H | H | red |
| 11 | H | —CH$_3$ | H | —CH$_3$ | H | —CH$_2$—⌬ | H | H | red |

TABLE I-continued

| Ex. | R | R₁ | R₄ | R₅ | R₆ | R₇ | R₈ | | Dye-shade on polyacrylonitrile |
|---|---|---|---|---|---|---|---|---|---|
| 12 | H | —CH₃ | H | —CH₃ | H | —C₂H₄—COC₂H₅ (O) | H | H | scarlet |
| 13 | H | —CH₃ | H | —CH₃ | H | —C₂H₄—O—C(=O)—C₆H₅ | H | H | red |
| 14 | H | —CH₃ | H | —CH₃ | H | —C₄H₉ | H | H | bluish-red |
| 15 | H | —C₂H₅ | H | —C₂H₅ | H | —C₂H₅ | H | H | " |
| 16 | H | —CH₃ | H | —CH₂—C₆H₅ | H | —C₂H₅ | H | H | " |
| 17 | H | —CH₃ | H | —C₂H₅ | H | —C₂H₅ | H | H | " |
| 18 | H | —CH₃ | H | —C₆H₅ | H | —C₂H₅ | H | H | strong bluish red |
| 19 | H | —CH₃ | H | —C₂H₄—C₆H₅ | H | —C₂H₅ | H | H | bluish-red |
| 20 | —CH₃ | —CH₃ | H | —CH₃ | H | —CH₃ | H | H | " |
| 21 | —CH₃ | —CH₃ | H | —CH₃ | H | —C₂H₅ | H | H | " |
| 22 | —CH₃ | —CH₃ | H | —CH₃ | H | —CH₂—C₆H₅ | H | H | " |
| 23 | —CH₃ | —CH₃ | H | —CH₃ | —CH₃ | —C₂H₅ | H | H | " |
| 24 | C₆H₅—CH₂— | —CH₃ | H | —CH₃ | H | —C₂H₅ | H | H | " |
| 25 | C₆H₅—CH₂— | —CH₃ | H | —CH₃ | H | —C₂H₅ | Cl | H | " |
| 26 | C₆H₅—CH₂— | —CH₃ | H | —CH₃ | H | —CH₃ | H | H | " |
| 27 | C₆H₅—CH₂— | —CH₃ | H | —CH₃ | H | —C₄H₉ | H | H | " |
| 28 | C₆H₅—CH₂— | —CH₃ | H | —CH₃ | —CH₃ | —C₂H₅ | H | H | " |
| 29 | C₆H₅—CH₂— | —C₂H₅ | H | —C₂H₅ | H | —C₂H₅ | H | H | " |
| 30 | C₆H₅— | —CH₃ | H | —CH₃ | H | —C₂H₅ | H | H | strong bluish-red |
| 31 | C₆H₅— | —CH₃ | H | —CH₃ | H | —C₂H₅ | Cl | H | " |
| 32 | C₆H₅— | —CH₃ | H | —CH₃ | H | —C₂H₅ | Cl | Cl | " |
| 33 | C₆H₅— | —CH₃ | H | —CH₃ | H | —CH₃ | H | H | " |
| 34 | C₆H₅— | —CH₃ | H | —CH₃ | H | —C₄H₉ | H | H | " |
| 35 | C₆H₅— | —C₂H₅ | H | —C₂H₅ | H | —C₂H₅ | H | H | " |
| 36 | C₆H₅— | —CH₃ | H | —CH₃ | —CH₃ | —C₂H₅ | H | H | " |
| 37 | C₆H₅— | —CH₃ | H | —C₆H₅ | H | —C₂H₅ | H | H | reddish-violet |
| 38 | H | —CH₃ | H | —CH₃ | H | —C₂H₅ | —NO₂ | H | bluish-red |
| 39 | H | —CH₃ | H | —CH₃ | H | —C₂H₅ | —CN | H | " |
| 40 | H | —CH₃ | H | —CH₃ | H | —C₂H₅ | —SO₂—C₆H₅ | H | " |
| 41 | H | —CH₃ | H | —CH₃ | H | —C₂H₅ | —SO₂NHCH₃ | H | " |
| 42 | H | —CH₃ | H | —CH₃ | H | —C₂H₅ | —SO₂—N(CH₃)₂ | H | " |
| 43 | H | —CH₃ | H | —CH₃ | H | —C₂H₅ | —CF₃ | | bluish-red |
| 44 | H | —CH₃ | H | —CH₃ | H | —C₂H₅ | —COOCH₃ | | " |
| 45 | H | —CH₃ | H | —CH₃ | H | —C₂H₅ | —CONHCH₃ | | " |
| 46 | H | —CH₃ | H | —CH₃ | H | —C₂H₅ | —O—CH₃ | | " |

TABLE I-continued

| Ex. | R | R₁ | R₄ | R₅ | R₆ | R₇ | R₈ | R₉ | Dye-shade on polyacrylonitrile |
|---|---|---|---|---|---|---|---|---|---|
| 47 | H | —CH₃ | H | —CH₃ | H | —C₂H₅ | —O—C₆H₅ | | " |
| 48 | H | —CH₃ | H | —CH₃ | H | —C₂H₅ | —O—CO—C₆H₅ | | " |
| 49 | H | —CH₃ | H | —CH₃ | H | —C₂H₅ | —N=N—C₆H₅ | | " |
| 50 | H | —CH₃ | H | —CH₃ | H | —C₂H₅ | —CH₂—C₆H₅ | | " |
| 51 | H | —CH₃ | H | —CH₃ | H | —C₂H₅ | —NH—CO—C₆H₅ | | " |
| 52 | H | —CH₃ | H | —CH₃ | H | —C₂H₅ | —O—CO—NH—C₆H₅ | | " |
| 53 | H | —CH₃ | H | —CH₃ | H | —C₂H₅ | —O—CO—N(CH₃)₂ | | " |
| 54 | H | —CH₃ | H | —CH₃ | H | —C₂H₅ | —O—CO—N(CH₃)—C₆H₅ | | " |
| 55 | H | —CH₃ | H | —CH₃ | H | —C₂H₅ | —SO₂—CH₃ | H | bluish-red |
| 56 | H | —CH₃ | H | —CH₃ | H | —C₂H₅ | —OSO₂—N(CH₃)₂ | H | " |
| 57 | H | —CH₃ | H | —CH₃ | H | —C₂H₅ | —CH₂—O—C₆H₅ | H | " |

| Ex. | | Dye shade on polyacrylonitrile |
|---|---|---|
| 58. | | bluish-red |
| 59. | | bluish-red |
| 60. | | bluish-red |
| 61. | | bluish-red |

| Ex. | | Dye shade on polyacrylonitrile |
|---|---|---|
| 62. | 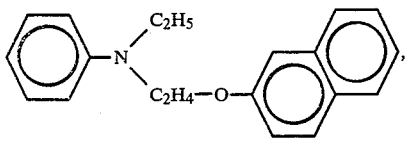 (structure with triazolium, azo, N(CH3)CH2-CH(CH3)-O-pentachlorophenyl, Cl⁻) | bluish-red |
| 63. | (structure with triazolium, azo, tolyl, N(C2H5)(C2H4-O-pentachlorophenyl), Cl⁻) | bluish-red |

EXAMPLES 64 AND 65

8.4 Parts 3-amino-1,2,4-triazole are dissolved in 22 parts 62% nitric acid and 18 parts water. The solution is mixed with 20 parts ice and is added dropwise, over a period of 20 minutes, to an aqueous solution of 4 N sodium nitrite. After 30 minutes the excess nitrite is decomposed with 0.4 parts aminosulphonic acid and the diazo solution, over a period of 20 minutes, is added dropwise to a solution containing 29.1 parts of the coupling component of the formula

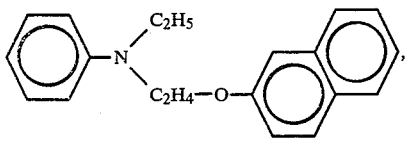

25 parts glacial acetic acid and 10 parts ice. The pH is adjusted to 4.0 to 4.5 with sodium hydroxide, the suspension is stirred for 15 hours and filtered to obtain the dye product. The dried dye is suspended in 100 parts benzene and 100 parts cyclohexane, stirred for 1 hour at 40° and filtered at room temperature.

31.8 Parts of the dried and ground dye are dissolved in 250 parts chloroform at 50° and are mixed with 6.5 parts magnesium oxide. Over a period of 10 minutes, 25 parts dimethyl sulphate are added dropwise and the mixture is stirred for 2 hours at 50° to 60°. After cooling to room temperature, the suspension is diluted with 250 parts chloroform and filtered onto "Hyflo". The chloroform phase is extracted three times with a total of 2000 parts of a 5% aqueous sodium chloride solution. The solvent is extracted under vacuum and the residue is dried over Glauber's salt. After dissolving the dye residue in 1000 parts water at 70° to 80°, 10 parts zinc chloride and 50 parts sodium chloride are added and after 20 hours of stirring the resulting dye is obtained by filtration.

After drying at 50° under vacuum, 31.2 parts of the dye of the formula

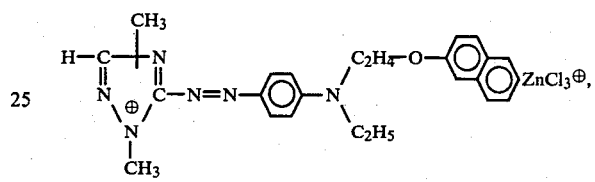

is obtained which gives a fast red shade on polyester fibres.

Using the coupling component of the formula

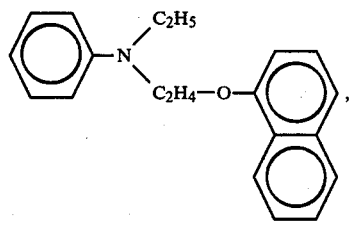

instead of the above-mentioned coupling component and employing the same procedure, the dye of the formula

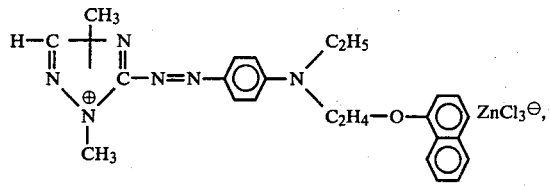

is obtained which when used in an acid dyebath gives the same red colour on polyacrylonitrile and acid-modified polyester fibres.

The coupling components used above may be prepared with good yields and purity by condensing N-ethyl-N-2'-chloroethylaniline with β-naphthol or α-naphthol at 110° to 120° without a solvent in the presence of a base, such as sodium hydroxide, and with a catalytic amount of calcium iodide.

The structural composition of further dyes is shown in the following Table II. They may be prepared in accordance with the procedure of Examples 64 and 65 and correspond with the formula

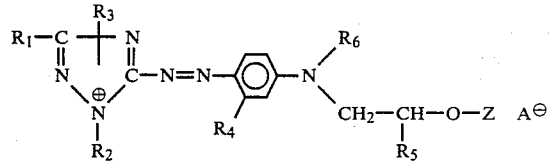

(b), in which $R_1$ to $R_6$ and Z have the significances as shown in the columns of the Table. A further column indicates the dye shade on polyacrylonitrile.

The anion $A^\ominus$ may be any one of those named in the foregoing description.

TABLE II

| Ex. | $R_1$ | $R_2$ | $R_3$ | $R_4$ | $R_5$ | $R_6$ | Z | Dye-shade on polyacrylonitrile |
|---|---|---|---|---|---|---|---|---|
| 66 | H | —CH₃ | —CH₃ | H | H | —CH₃ | naphthyl | bluish-red |
| 67 | H | —CH₃ | —CH₃ | H | H | —CH₃ | naphthyl | " |
| 68 | H | —CH₃ | —CH₃ | H | —CH₃ | —CH₃ | naphthyl | " |
| 69 | H | —CH₃ | —CH₃ | H | —CH₃ | —CH₃ | naphthyl | " |
| 70 | H | —CH₃ | —CH₃ | —CH₃ | H | —C₂H₅ | naphthyl | " |
| 71 | H | —CH₃ | —CH₃ | —CH₃ | H | —C₂H₅ | naphthyl | " |
| 72 | H | —CH₃ | —CH₃ | —CH₃ | —CH₃ | —C₂H₅ | naphthyl | " |
| 73 | H | —CH₃ | —CH₃ | —CH₃ | —CH₃ | —C₂H₅ | naphthyl | " |
| 74 | H | —CH₃ | —CH₃ | H | H | —C₄H₉ | naphthyl | bluish-red |
| 75 | H | —CH₃ | —CH₃ | Cl | H | —C₂H₅ | naphthyl | scarlet |
| 76 | H | —C₂H₅ | —C₂H₅ | H | H | —C₂H₅ | naphthyl | bluish-red |
| 77 | H | —C₂H₅ | —C₂H₅ | H | H | —C₂H₅ | naphthyl | " |
| 78 | H | —C₂H₅ | —C₂H₅ | H | —CH₃ | —CH₃ | naphthyl | " |
| 79 | H | —C₂H₅ | —C₂H₅ | H | —CH₃ | —CH₃ | naphthyl | " |
| 80 | H | —CH₃ | —CH₂—C₆H₅ | H | H | —C₂H₅ | naphthyl | red |
| 81 | H | —CH₃ | —CH₂—C₆H₅ | H | H | —C₂H₅ | naphthyl | red |
| 82 | —CH₃ | —CH₃ | —CH₃ | H | H | —C₂H₅ | naphthyl | bluish-red |
| 83 | —CH₃ | —CH₃ | —CH₃ | H | H | —C₂H₅ | naphthyl | bluish-red |
| 84 | —C₆H₅ | —CH₃ | —CH₃ | H | H | —C₂H₅ | naphthyl | strong bluish-red |

TABLE II-continued

| Ex. | R₁ | R₂ | R₃ | R₄ | R₅ | R₆ | Z | Dye-shade on polyacrylonitrile |
|---|---|---|---|---|---|---|---|---|
| 85 |  | —CH₃ | —CH₃ | H | H | —C₂H₅ |  | strong bluish-red |
| 86 |  | —CH₃ | —CH₃ | H | —CH₃ | —C₂H₅ |  | strong bluish-red |
| 87 |  | —CH₃ | —CH₃ | H | —CH₃ | —C₂H₅ |  | strong bluish-red |
| 88 |  | —CH₃ | —CH₃ | —CH₃ | H | —C₂H₅ |  | strong bluish-red |
| 89 |  | —CH₃ | —CH₃ | —CH₃ | H | —C₂H₅ |  | strong bluish-red |
| 90 |  |  | —CH₃ | H | H | —C₂H₅ |  | strong bluish-red |
| 91 |  |  | —CH₃ | H | H | —C₂H₅ |  | strong bluish-red |
| 92 | H |  | —CH₃ | H | H | —C₂H₅ |  | bluish-red |
| 93 | H | —CH₂CH₂OH | —C₂H₄OH | H | H | —C₂H₅ |  | " |
| 94 | H | —CH₂CH₂OH | —C₂H₄OH | H | H | —C₂H₅ |  | " |
| 95 | H | —CH₂—CH—OH<br>　　　\|<br>　　　CH₃ | —CH₂—CH—OH<br>　　　\|<br>　　　CH₃ | H | H | —C₂H₅ |  | " |
| 96 | H | —CH₂—CH—OH<br>　　　\|<br>　　　CH₃ | —CH₂—CH—OH<br>　　　\|<br>　　　CH₃ | H | H | —C₂H₅ |  | " |
| 97 | H | —C₂H₄CONH₂ | —C₂H₄CONH₂ | H | H | —C₂H₅ |  | " |
| 98 | H | —C₂H₄CONH₂ | —C₂H₄CONH₂ | H | H | —C₂H₅ |  | " |
| 99 | H | —CH₃ | —CH₃ | H |  | —C₂H₅ |  | " |
| 100 | H | —CH₃ | —CH₃ | H |  | —C₂H₅ |  | bluish-red |
| 101 |  | —CH₃ | —CH₃ | —OCH₃ | H | —C₂H₅ |  | " |
| 102 |  | —CH₃ | —CH₃ | H | H | —C₂H₅ |  | " |
| 103 |  | —CH₃ | —CH₃ | H | H | —C₂H₅ |  | " |

EXAMPLE 104

18 Parts 2-amino-6-methoxybenzothiazole are dissolved in 100 parts glacial acetic acid and 90 parts sulphuric acid are added thereto with ice cooling so that the temperature does not rise above 35° to 40°. Finally, 100 parts ice are added and, at a temperature between −5° and 0°, a solution consisting of 7.3 parts sodium nitrite and 25 parts water is added dropwise. The mixture is stirred, with cooling, for 1 hour and thereupon it is mixed with a solution containing 24.1 parts of a coupling component of the formula

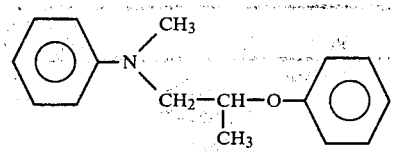

dissolved in 25 parts glacial acetic acid. The reaction mixture is stirred at room temperature for 3 hours and then the pH is adjusted to 3 with 170 parts of a 30% aqueous solution of sodium hydroxide and the temperature is kept under 35° by cooling. The resulting dye is filtered, washed thoroughly with water and dried under vacuum at 50°.

21.5 Parts of the dried and ground dye are stirred with 200 parts glacial acetic acid, mixed with 2.2 parts magnesium oxide and the mixture is heated to 60° to 70°. Over a period of 15 minutes, 14 parts dimethylsulphate are added dropwise and the mixture is stirred for 3 hours at 70° to 75°. The reaction mixture is diluted with 2000 parts water and the dye is salted out with 15 parts zinc chloride and 80 parts sodium chloride. It is filtered, washed with 100 parts of a 5% aqueous solution of sodium chloride and dried at 50° under vacuum 23.8 Parts of the dye of the formula

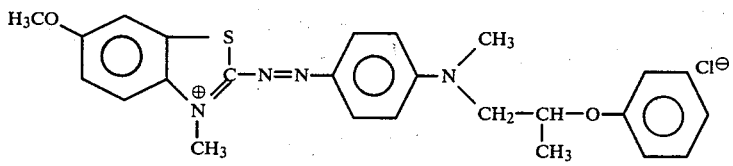

are obtained which on polyacrylonitrile and acid-modified polyester fibres gives fast dyeings of a pure blue colour.

EXAMPLE 105

Instead of the last-mentioned coupling component, the coupling component of the formula

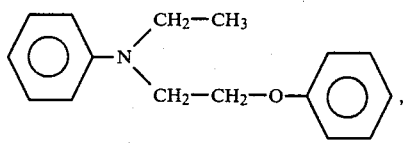

is used a similar dye of the formula

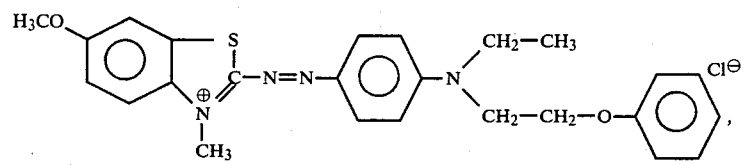

is obtained which likewise gives fast dyeings of a blue shade on polyacrylonitrile and acid-modified polyester fibres.

The structural composition of further dyes is shown in the following Table III. The dyes can be obtained in accordance with the procedure of the foregoing Examples and correspond with the formula

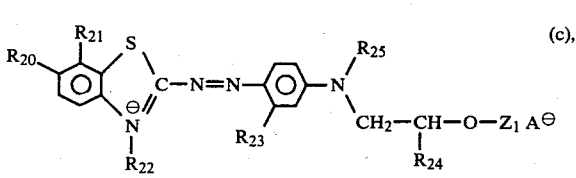

(c), in which $R_{20}$ to $R_{25}$ and $Z_1$ have the significances as shown in the columns of the Table. The anion $A^\ominus$ may be any one of those named in the foregoing description.

| Ex. | $R_{20}$ | $R_{21}$ | $R_{22}$ | $R_{23}$ | $R_{24}$ | $R_{25}$ | $Z_1$ | Dye-shade on polyacrylonitrile |
|---|---|---|---|---|---|---|---|---|
| 106 | H | H | —CH$_3$ | H | H | —C$_2$H$_5$ | ⌬ | blue |
| 107 | H | H | —CH$_3$ | —CH$_3$ | H | —C$_2$H$_5$ | ⌬ | " |
| 108 | H | H | —CH$_3$ | H | H | —C$_2$H$_5$ | naphthyl | " |
| 109 | H | H | —CH$_3$ | H | —CH$_3$ | —CH$_3$ | ⌬ | " |
| 110 | CH$_3$O— | H | —CH$_3$ | H | H | —CH$_3$ | ⌬ | " |

-continued

| Ex. | $R_{20}$ | $R_{21}$ | $R_{22}$ | $R_{23}$ | $R_{24}$ | $R_{25}$ | $Z_1$ | Dye-shade on polyacrylonitrile |
|---|---|---|---|---|---|---|---|---|
| 111 | $CH_3O-$ | H | $-CH_3$ | H | H | $-C_2H_5$ |  | " |
| 112 | $CH_3O-$ | H | $-CH_3$ | H | H | $-C_2H_5$ |  | greenish-blue |
| 113 | $CH_3O-$ | H | $-CH_3$ | H | H | $-C_2H_5$ |  | greenish-blue |
| 114 | $CH_3O-$ | H | " | H | H | $-C_2H_5$ |  | " |
| 115 | $CH_3O-$ | H | " | H | H | $-C_2H_5$ |  | " |
| 116 | $CH_3O-$ | H | " | H | H | $-C_2H_5$ |  | " |
| 117 | $CH_3O-$ | H | " | H | H | $-C_2H_5$ |  | " |
| 118 | $CH_3O-$ | H | $-C_2H_5CONH_2$ | H | H | $-C_2H_5$ |  | " |
| 119 | $CH_3O-$ | H | $-C_2H_4OH$ | H | H | $-C_2H_5$ |  | " |
| 120 | $CH_3-O-$ | H | $-CH_2-\overset{OH}{\underset{\phantom{x}}{C}H}-CH_2$ | H | H | $-C_2H_5$ |  | greenish-blue |
| 121 | " | H | $-C_2H_5$ | H | H | $-C_2H_5$ |  | " |
| 122 | " | H | $-C_2H_5$ | H | $-CH_3$ | $-CH_3$ |  | " |
| 123 | " | H | $-CH_3$ | $-CH_3$ | H | $-C_2H_5$ |  | blue |
| 124 | " | H | $-CH_3$ | $-CH_3$ | $-CH_3$ | $-CH_3$ |  | " |
| 125 | " | H | $-CH_3$ | H | H | $-C_2H_5$ |  | greenish-blue |
| 126 | " | H | $-CH_3$ | Cl | H | $-C_2H_5$ |  | blue |
| 127 | " | H | $-CH_3$ | $CH_3O-$ | H | $-C_2H_5$ |  | " |
| 128 | $-O-CH_2-O-$ | | $-CH_3$ | H | H | $-C_2H_5$ |  | blue |
| 129 | $-CH_3$ | $-CH_3$ | $-CH_3$ | H | H | $-C_2H_5$ |  | " |
| 130 | Cl | H | $-CH_3$ | H | H | $-C_2H_5$ |  | greenish-blue |
| 131 | $-CH_3$ | H | $-CH_3$ | H | H | $-C_2H_5$ |  | blue |
| 132 | 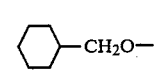 | " | $-CH_3$ | H | H | $-C_2H_5$ |  | greenish-blue |
| 133 | $CH_3-\underset{\underset{O}{\|}}{C}-$ | " | $-CH_3$ | H | H | $-C_2H_5$ |  | " |

-continued

| Ex. | $R_{20}$ | $R_{21}$ | $R_{22}$ | $R_{23}$ | $R_{24}$ | $R_{25}$ | $Z_1$ | Dye-shade on polyacrylonitrile |
|---|---|---|---|---|---|---|---|---|
| 134 | $CH_3-\underset{\underset{O}{\|\|}}{C}-NH-$ | " | $-CH_3$ | H | H | $-C_2H_5$ |  | " |
| 135 | 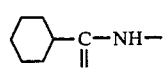 | " | $-CH_3$ | H | H | $-C_2H_5$ |  | " |
| 136 | $CH_3-SO_2-NH-$ | H | $-CH_3$ | H | H | $-C_2H_5$ |  | greenish-blue |
| 137 | $(CH_3)_2N-SO_2-$ | " | $-CH_3$ | H | H | $-C_2H_5$ |  | " |
| 138 | $R_{20}$ together with $R_{21}$ | | $-CH_3$ | H | H | $-C_2H_5$ |  | " |
| 139 | $\begin{array}{l}CH=CH-\\ \|\\ CH=CH-\\ R_{20}\text{ together}\\ \text{with }R_{21}\end{array}$ | | $-CH_3$ | H | H | $-CH_3$ |  | " |
| 140 | $\begin{array}{l}CH=CH-\\ \|\\ CH=CH-\\ \end{array}$ 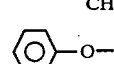$-O-$ | H | $-CH_3$ | H | H | $-C_2H_5$ |  | " |
| 141 | 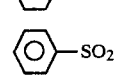$-SO_2-$ | " | $-CH_3$ | H | H | $-C_2H_5$ |  | " |

EXAMPLE 142

By diazotizing 33 parts 2-aminopyridine-N-oxide and coupling with a solution of 87.3 parts N-ethyl-N-2′β-naphthyloxyethylaniline in dimethylformamide, (at the same time removing the oxygen atom of the N-oxide group), according to known methods such as, for example, those described in U.S. Pat. No. 3,051,697 there is obtained 25 parts of the dye of the formula

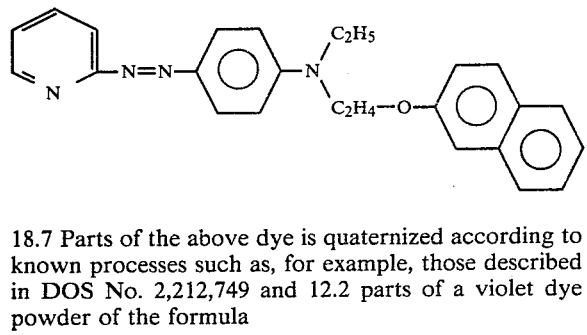

18.7 Parts of the above dye is quaternized according to known processes such as, for example, those described in DOS No. 2,212,749 and 12.2 parts of a violet dye powder of the formula

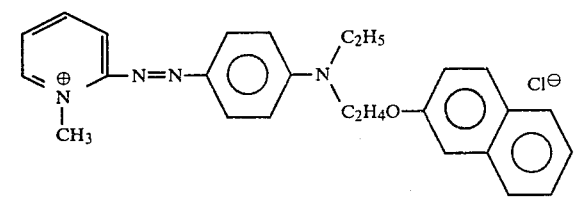

are obtained which on polyacrylonitrile or on acid-modified polyester fibres gives a fast reddish violet dyeing.

Using the coupling component of the formula

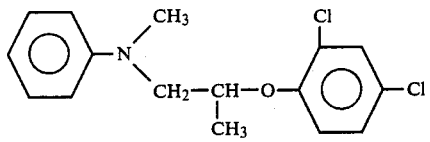

and employing a similar procedure, the dye of the formula

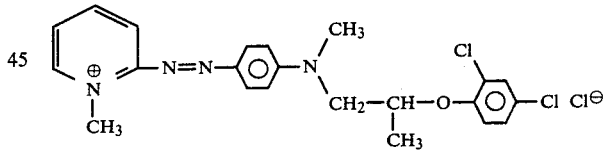

is obtained, which on polyacrylonitrile or on acidmodified polyester fibres gives fast dyeings of a reddish-violet shade.

The structural composition of further dyes is shown in the following Table IV. The dyes can be prepared in accordance with the procedure of the foregoing Examples and agree with the formula

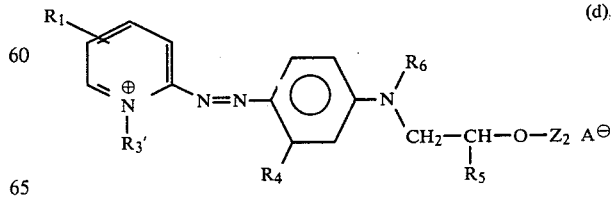

(d)

in which $R_1$, $R_4$, $R_5$, $R_6$, $R_3'$ and $Z_2$ have the significances as shown in the columns of the table. The anion $A^\ominus$ may be any one of those named in the foregoing description.

TABLE IV

| Ex. | $R_1$ | $R_3'$ | $R_4$ | $R_5$ | $R_6$ | $Z_2$ | Dye-shade on polyacrylonitrile |
|---|---|---|---|---|---|---|---|
| 144 | H | —CH$_3$ | H | H | —C$_2$H$_5$ | phenyl | reddish-violet |
| 145 | H | —CH$_3$ | H | H | —C$_2$H$_5$ | 2,5-dichlorophenyl | " |
| 146 | H | —CH$_3$ | H | H | —C$_2$H$_5$ | 1-methylnaphthyl | " |
| 147 | H | —CH$_3$ | H | —CH$_3$ | —CH$_3$ | 1-methylnaphthyl | " |
| 148 | H | —CH$_3$ | H | —CH$_3$ | —CH$_3$ | naphthyl | " |
| 149 | H | —CH$_3$ | H | —CH$_3$ | —CH$_3$ | phenyl | " |
| 150 | H | —CH$_3$ | —CH$_3$ | H | —C$_2$H$_5$ | phenyl | " |
| 151 | H | —CH$_3$ | —CH$_3$ | H | —C$_2$H$_5$ | naphthyl | " |
| 152 | —CH$_3$ | —CH$_3$ | H | H | —C$_2$H$_5$ | phenyl | " |
| 153 | H | —CH$_3$ | H | H | —C$_2$H$_5$ | pentachlorophenyl | violet |
| 154 | H | —CH$_3$ | H | H | —C$_2$H$_5$ | 2,3,5,6-tetrachlorophenyl | " |
| 155 | H | —C$_2$H$_5$ | H | H | —C$_2$H$_5$ | phenyl | reddish-violet |
| 156 | H | —C$_2$H$_5$ | H | H | —C$_2$H$_5$ | naphthyl | " |
| 157 | H | —OCH$_3$ | H | H | —C$_2$H$_5$ | phenyl | " |

| Ex. | | Dye-shade on polyacrylonitrile |
|---|---|---|
| 158. | (CH$_3$)$_2$NSO$_2$-substituted indazolium azo compound with —N(C$_2$H$_5$)(C$_2$H$_4$—O—naphthyl), Cl$^\ominus$ | violet |
| 159. | indazolium azo compound with —NH— naphthyl—N(H)(C$_2$H$_4$—O—phenyl), Cl$^\ominus$ | blue |

| | Dye-shade on polyacrylonitrile |
|---|---|
| Ex. | |
| 160. 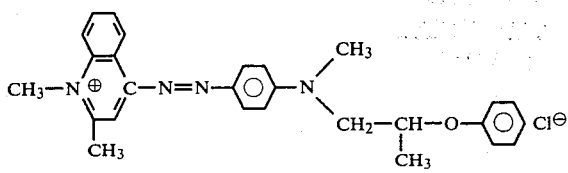 | blue |

Formulae of representative dyes of the foregoing Examples are as follows:

Example 1
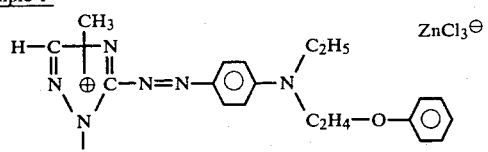

Example 3
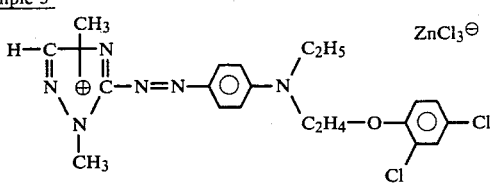

Example 58
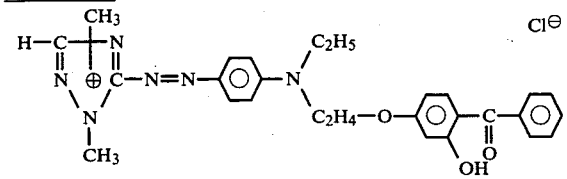

Example 61
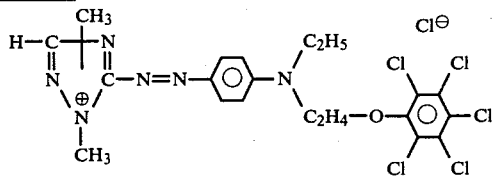

Example 64
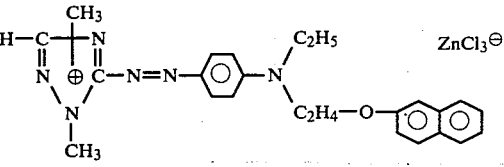

Example 65
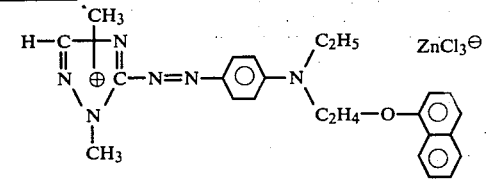

Example 104
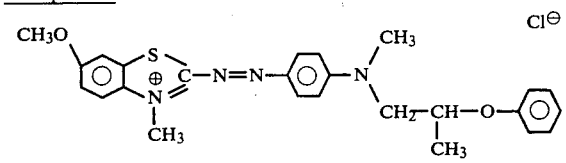

Example 142
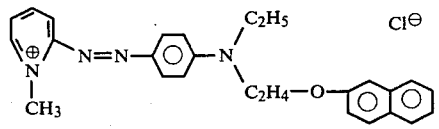

Example 142
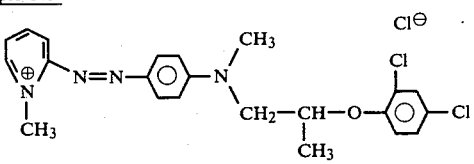

What is claimed is:
1. A compound of the formula

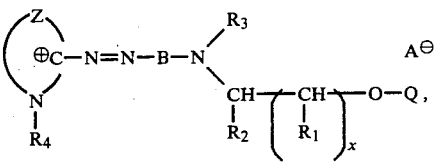

wherein each $R_1$ and $R_2$ is independently hydrogen; alkyl of 1 to 4 carbon atoms; alkyl of 1 to 4 carbon atoms substituted by halo, alkoxy of 1 to 4 carbon atoms or phenoxy; phenyl or cycloalkyl of 5 to 6 carbon atoms, $R_3$ is hydrogen, phenyl, alkyl of 1 to 12 carbon atoms or alkyl of 1 to 12 carbon atoms substituted by halo, alkoxy, cyano, phenyl, phenoxy, alkoxycarbonyl wherein the alkoxy radical has 1 to 4 carbon atoms, alkylcarbonyloxy wherein the alkyl radical has 1 to 4 carbon atoms, alkoxy of 1 to 4 carbon atoms, benzoyloxy, —O—CO—N(Ra)$_2$ or —CO—N(-RA)$_2$, wherein each Ra is independently hydrogen or alkyl of 1 to 4 carbon atoms, $R_4$ is alkyl of 1 to 8 carbon atoms; alkyl of 1 to 8 carbon atoms substituted by halo, hydroxy, cyano, phenyl, phenoxy, cycloalkyl of 5 or 6 carbon atoms, alkoxy of 1 to 4 carbon atoms or carbamoyl; alkenyl of 2 to 8 carbon atoms; alkenyl of 2 to 8 carbon atoms substituted by halo, hydroxy, cyano, phenyl, phenoxy, cycloalkyl of 5 to 6 carbon atoms, alkoxy of 1 to 4 carbon atoms or carbamoyl; alkoxy of 1 to 4 carbon atoms; alkoxy of 1 to 4 carbon atoms substituted by halo, hydroxy, cyano, phenyl, phenoxy, cycloalkyl of 5 to 6 carbon atoms, alkoxy of 1 to 4 carbon atoms or carbamoyl; cycloalkyl of 5 or 6 carbon atoms; cycloalkyl of 5 or 6 carbon atoms substituted by alkyl of 1 to 4 carbon atoms or

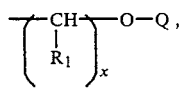

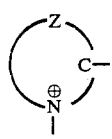

is triazolium, benzothiazulium or naphthothiazolium, or a substituted derivative thereof, wherein each substituent is independently alkyl of 1 to 4 carbon atoms; alkyl of 1 to 4 carbon atoms substituted by phenyl, hydroxy, carbamoyl, cycloalkyl of 5 to 6 carbon atoms, cyano or halo; halo; nitro; cyano; trifluoromethyl; alkoxy of 1 to 4 carbon atoms; alkoxy of 1 to 4 carbon atoms substituted by phenyl, hydroxy, carbamoyl, cycloalkyl of 5 or 6 carbon atoms, cyano or halo; cycloalkyl of 5 or 6 carbon atoms; cycloalkyl of 5 or 6 carbon atoms substituted by alkyl of 1 to 4 carbon atoms, alkoxy of 1 to 4 carbon atoms or halo; phenyl; phenyl substituted by cyano, nitro, alkyl of 1 to 4 carbon atoms, alkoxy of 1 to 4 carbon atoms or halo; phenoxy; phenoxy substituted by cyano, nitro, alkyl of 1 to 4 carbon atoms, alkoxy of 1 to 4 carbon atoms or halo; phenylazo; —CO—Ro; —CO—O—Ro; —CO—NH—Ro; —CO—N(Ro)$_2$; —NH—CO—Ro; —SO$_2$—Ro; —SO$_2$—NH—Ro; —SO$_2$—N(Ro)$_2$ or —NH—SO$_2$—Ro, wherein each Ro is independently alkyl of 1 to 4 carbon atoms or phenyl, with the proviso that the azo group is linked to a carbon atom of the ring containing the quaternized nitrogen atom, B is phenylene, substituted phenylene having 1 or 2 substituents, naphthylene or substituted naphthylene having 1 or 2 substituents, wherein each substituent of substituted phenylene and substituted naphthylene is independently alkoxy of 1 to 4 carbon atoms, alkyl of 1 to 4 carbon atoms or halo, each Q is independently

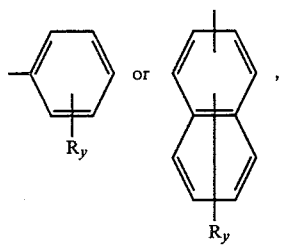

wherein each
R is independently hydroxy; halo; alkyl of 1 to 4 carbon atoms; alkyl of 1 to 4 carbon atoms substituted by halo, hydroxy, cyano, phenyl or phenoxy; alkoxy of 1 to 4 carbon atoms; alkoxy of 1 to 4 carbon atoms substituted by halo, hydroxy, cyano, phenyl or phenoxy; trihalomethyl; trifluoromethyl; cycloalkyl of 5 or 6 carbon atoms; cycloalkyl of 5 or 6 carbon atoms substituted by alkyl of 1 to 4 carbon atoms; cyano; nitro; phenoxy; naphthyloxy; phenylazo; —CO—Ro; —CO—O—Ro; —CO—NH—Ro; —CO—N(Ro)$_2$; —O—CO—Ro; —O—CO—NH—Ro; —O—CO—N(Ro)$_2$; —NH—CO—Ro; —SO$_2$—Ro; —SO$_2$—NH—Ro; —SO$_2$—N(Ro)$_2$; —OSO$_2$—N(Ro)$_2$;

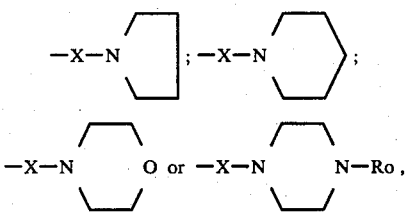

wherein each
Ro is independently alkyl of 1 to 4 carbon atoms or phenyl, and
X is —CO— or —SO$_2$—, and
y is 0, 1, 2, 3, 4 or 5, each x is independently 1, 2 or 3, and
A$^\ominus$ is an anion, wherein each halo is independently chloro, bromo or iodo.

2. A compound according to claim 1 wherein each
R$_1$ is independently hydrogen, alkyl of 1 to 4 carbon atoms or phenyl,
R$_2$ is hydrogen,
R$_3$ is hydrogen, alkyl of 1 to 4 carbon atoms or alkyl of 1 to 4 carbon atoms substituted by phenoxy, phenyl, alkoxycarbonyl wherein the alkoxy radical has 1 to 4 carbon atoms or benzoyloxy,
R$_4$ is alkyl of 1 to 4 carbon atoms, alkyl of 1 to 4 carbon atoms substituted by phenyl, hydroxy or carbamoyl or alkoxy of 1 to 4 carbon atoms,

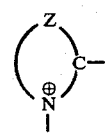

is triazolium or benzothiazolium, or a substituted derivative thereof,
B is

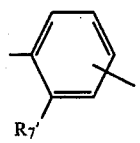

or naphthylene,
wherein R$_7'$ is hydrogen, halo, alkyl of 1 to 4 carbon atoms or alkoxy of 1 to 4 carbon atoms,
Q is

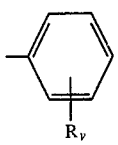

or naphthyl,
   wherein y is 0, 1, 2, 3, 4 or 5, with the proviso that each R is halo when y is 3, 4 or 5.

3. A compound according to claim 2 wherein $A^\ominus$ is chloride, $ZnCl_3^\ominus$, methylsulfate or acetate.

4. A compound according to claim 2 wherein

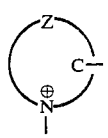

is triazolium or substituted triazolium.

5. A compound according to claim 2 wherein each
   $R_1$ is independently hydrogen, methyl or phenyl,
   $R_2$ is hydrogen,
   $R_3$ is methyl, ethyl, butyl, phenoxyethyl, benzyl, ethoxycarbonylethyl or benzoyloxyethyl,
   $R_4$ is methyl, ethyl, benzyl, 2-hydroxyethyl, 2-hydroxypropyl, 2-carbamoylethyl or methoxy,
   B is

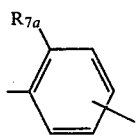

or naphthylene,
   wherein $R_{7a}$ is hydrogen, methyl, methoxy or chloro,
   Q is

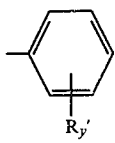

or naphthyl,
   wherein each
      R' is independently chloro, alkyl of 1 to 4 carbon atoms, benzyl, nitro, cyano, phenylsulfonyl, methylsulfamoyl, dimethylsulfamoyl, trifluoromethyl, methoxycarbonyl, methylcarbamoyl, methoxy, phenoxy, benzoyloxy, phenylazo, benzamido, phenylcarbamoyloxy, dimethylcarbamoyloxy, N-methyl-n-phenylcarbamoyloxy, methylsulfonyl, dimethylsulfamoyloxy, phenoxymethyl, benzoyl or hydroxy, and
      y is 0, 1, 2, 3, 4 or 5, with the proviso that each R' is chloro if y is 3, 4 or 5, and
      x is 1 or 2.

6. A compound according to claim 5 with the proviso that each R' is chloro or one R' is hydroxy and the other is benzoyl if y is 2 and each R' is chloro if v is 3, 4 or 5.

7. A compound according to claim 5 wherein

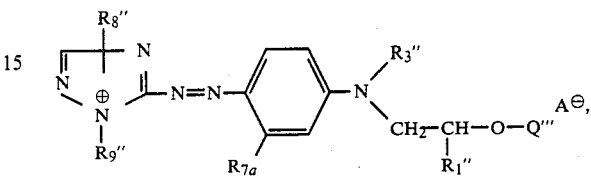

is triazolium or substituted triazolium.

8. A compound according to claim 7 having the formula

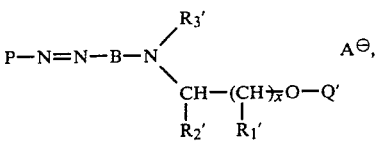

wherein
   $R_1''$ is hydrogen, methyl or phenyl,
   $R_3''$ is methyl, ethyl, butyl, ethoxycarbonylethyl or benzyl,
   $R_{7a}$ is hydrogen, methyl, methoxy or chloro,
   each of $R_8''$ and $R_9''$ is independently methyl, ethyl, 2-hydroxyethyl, 2-hydroxypropyl, 2-carbamoylethyl, benzyl, 2-phenylethyl or cyclohexyl,
   $Q'''$ is phenyl, naphthyl or phenyl substituted by methyl, chloro, methylsulfonyl or phenylsulfonyl, and
   $A^\ominus$ is an anion.

9. A compound according to claim 8 wherein $R_1''$ is hydrogen.

10. A compound according to claim 9 wherein each of $R_3''$, $R_8''$ and $R_9''$ is independently methyl, ethyl or benzyl.

11. A compound according to claim 10 wherein
   $R_8''$ is methyl, and
   $R_9''$ is methyl.

12. A compound according to claim 8 wherein each of $R_8''$ and $R_9''$ is independently methyl, ethyl or benzyl.

13. A compound according to claim 1 having the formula

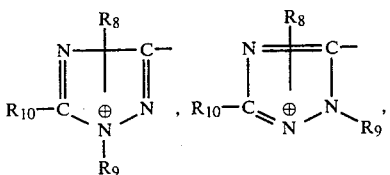

wherein P is

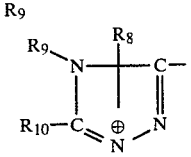

-continued

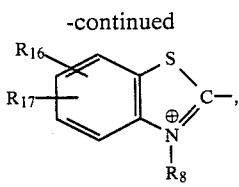

wherein
R₈ is alkyl of 1 to 4 carbon atoms; alkyl of 1 to 4 carbon atoms substituted by hydroxy, halo, cyano, phenyl or carbamoyl; alkenyl of 2 to 4 carbon atoms; alkenyl of 2 to 4 carbon atoms substituted by hydroxy, halo, cyano, phenyl or carbamoyl; cyclohexyl or cyclohexyl substituted by alkyl of 1 to 4 carbon atoms, R₉ is alkyl of 1 to 4 carbon atoms; alkyl of 1 to 4 carbon atoms substituted by hydroxy, halo, cyano, phenyl or carbamoyl; cyclohexyl; cyclohexyl substituted by alkyl of 1 to 4 carbon atoms; phenyl or phenyl substituted by halo, alkyl of 1 to 4 carbon atoms or alkoxy of 1 to 4 carbon atoms, R₁₀ is hydrogen or a significance of R₉, and each of R₁₆ and R₁₇ is independently hydrogen; halo; alkyl of 1 to 4 carbon atoms; alkyl of 1 to 4 carbon atoms substituted by phenyl, hydroxy, carbamoyl, cycloalkyl of 5 or 6 carbon atoms, cyano or halo; alkoxy of 1 to 4 carbon atoms; alkoxy of 1 to 4 carbon atoms substituted by phenyl, hydroxy, carbamoyl, cycloalkyl of 5 or 6 carbon atoms, cyano or halo; phenoxy; —CO—Ro; —CO—O—Ro; —CO—NH—Ro; —CO—N(Ro)₂; —NH—CO—Ro; —SO₂—Ro; —SO₂—NH—Ro; —SO₂—N(Ro)₂ or —NH—SO₂—Ro, wherein each Ro is independently alkyl of 1 to 4 carbon atoms or phenyl, or R₁₆ and R₁₇ are on adjacent carbon atoms and taken together are —CH=CH—CH=CH—, each R₁' and R₂' is independently hydrogen, phenyl or alkyl of 1 to 4 carbon atoms, R₃' is hydrogen, alkyl of 1 to 4 carbon atoms or alkyl of 1 to 4 carbon atoms substituted by phenyl, halo, alkoxy of 1 to 4 carbon atoms, phenoxy, alkylcarbonyloxy wherein the alkyl radical has 1 to 4 carbon atoms, benzoyloxy, cyano or dialkylcarbamoyl wherein each alkyl radical independently has 1 to 4 carbon atoms, B is

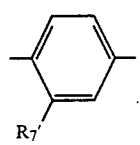

or naphthylene,
wherein R₇' is hydrogen, halo, alkyl of 1 to 4 carbon atoms or alkoxy of 1 to 4 carbon atoms, Q' is

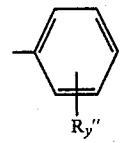

or naphthyl,
wherein each R″ is independently nitro; halo; hydroxy; cyano; trihalomethyl; trifluoromethyl; alkyl of 1 to 4 carbon atoms; alkyl of 1 to 4 carbon atoms substituted by phenyl or phenoxy; alkoxy of 1 to 4 carbon atoms; alkoxy of 1 to 4 carbon atoms substituted by phenyl or phenoxy; phenoxy; phenylazo; cyclohexyl; benzoyloxy; phenylcarbamoyloxy; —CO—Ro; —CO—O—Ro; —CO—NH—Ro; —CO—N(Ro)₂; —NH—CO—Ro; —SO₂—Ro; —SO₂—NH—Ro; —SO₂—N(Ro)₂; —O—CO—N(Ro)₂; —O—SO₂—N(Ro)₂;

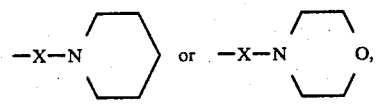

wherein each
Ro is independently alkyl of 1 to 4 carbon atoms or phenyl, and
X is —CO— or —SO₂—, and
y is 0, 1, 2, 3, 4 or 5, with the proviso that each R″ is halo when y is 3, 4 or 5,
x is 1, 2 or 3, and
A⊖ is an anion.

14. A compound according to claim 13 wherein P is

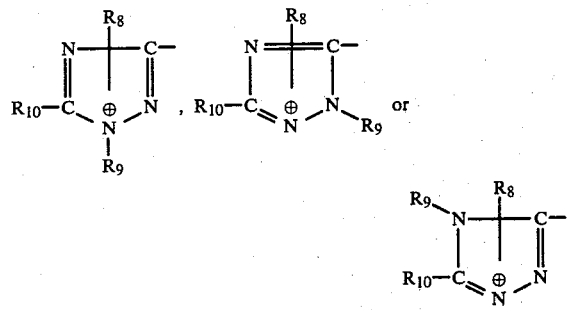

15. A compound according to claim 14 wherein
R₈ is alkyl of 1 to 4 carbon atoms or alkyl of 1 to 4 carbon atoms monosubstituted by phenyl, hydroxy or carbamoyl,
R₉ is alkyl of 1 to 4 carbon atoms or alkyl of 1 to 4 carbon atoms monosubstituted by phenyl, hydroxy or carbamoyl, and
R₁₀ is hydrogen, alkyl of 1 to 4 carbon atoms or alkyl of 1 to 4 carbon atoms monosubstituted by phenyl.

16. A compound according to claim 15 wherein
R₁' is hydrogen or alkyl of 1 to 4 carbon atoms,
R₂' is hydrogen,
R₃' is alkyl of 1 to 4 carbon atoms or alkyl of 1 to 4 carbon atoms monosubstituted by phenoxy,
B is

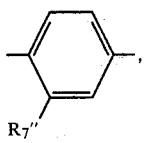

wherein
R7'' is hydrogen, alkyl of 1 to 4 carbon atoms or alkoxy of 1 to 4 carbon atoms,
Q' is

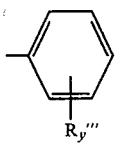

or naphthyl,
wherein each R''' is independently halo; nitro; cyano; phenylsulfonyl; alkoxy of 1 to 4 carbon atoms; benzoyl; phenoxy; benzoyloxy; phenylazo; benzamido; phenylcarbamoyloxy; trifluoromethyl; alkyl of 1 to 4 carbon atoms; alkyl of 1 to 4 carbon atoms monosubstituted by phenyl; —CO—O—Rz; —CO—NH—Rz; —SO₂—Rz; —SO₂—NH—Rz; —SO₂—N(Rz)₂; —O—CO—N(Rz)₂; —O—CO—NRz—phenyl or —O—SO₂—N(Rz)₂,
wherein each Rz is independently alkyl of 1 to 4 carbon atoms, and
y is 0, 1, 2, 3, 4 or 5, with the proviso that each R'' is chloro if y is 3, 4 or 5, and
x is 1.

17. A compound according to claim 16 wherein A⊖ is chloride, ZnCl₃⊖, methylsulfate or acetate.

18. A compound according to claim 16 wherein
R₈ is methyl,
R₉ is methyl, and
R₁₀ is hydrogen.

19. A compound according to claim 18 wherein
R₂' is hydrogen,
R₃' is methyl or ethyl,
R₇'' is hydrogen, and
Q' is

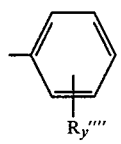

or 2-naphthyl,
wherein each
R'''' is nitro, cyano, phenylsulfonyl, methylsulfamoyl, dimethylsulfamoyl, methoxycarbonyl, methylcarbamoyl, methoxy, phenoxy, benzoyloxy, phenylazo, benzamido, phenylcarbamoyloxy, dimethylcarbamoyloxy, N-methyl-N-phenylcarbamoyloxy, methylsulfonyl, dimethylsulfamoyloxy, trifluoromethyl, methyl, benzyl or chloro, and
y is 0, 1, 2, 3, 4 or 5, with the proviso that each R is chloro if y is 2, 3, 4 or 5.

20. A compound according to claim 19 with the proviso that when y is 1, R'''' is in the 4-position.

21. A compound according to claim 19 wherein A⊖ is chloride, ZnCl₃⊖, methylsulfate or acetate.

22. A compound according to claim 13 wherein P is

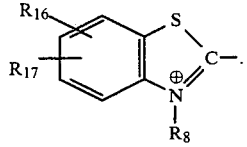

23. A compound according to claim 22 wherein
R₈ is alkyl of 1 to 4 carbon atoms or alkyl of 1 to 4 carbon atoms monosubstituted by carbamoyl, and
each of R₁₆ and R₁₇ is independently hydrogen; alkoxy of 1 to 4 carbon atoms; alkoxy of 1 to 4 carbon atoms monosubstituted by phenyl; benzamido; phenoxy; phenylsulfonyl; —CO—Rz; —CO—N-H—Rz or —NH—SO₂—Rz; wherein each Rz is independently alkyl of 1 to 4 carbon atoms, or
R₁₆ and R₁₇ are on adjacent carbon atoms and taken together are —CH=CH—CH=CH—.

24. A compound according to claim 23 wherein
R₁' is hydrogen or methyl,
R₂' is hydrogen,
R₃' is methyl or ethyl,
B is

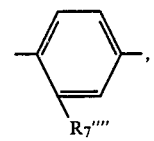

wherein R₇'''' is hydrogen or methyl,
Q' is

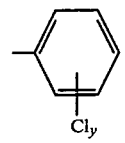

or naphthyl,
wherein y is 0, 1, 2, 3, 4 or 5, and
x is 1.

25. A compound according to claim 22 having the formula

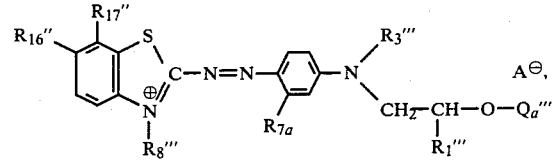

wherein
R₁''' is hydrogen or methyl,
R₃''' is methyl or ethyl,
R₇ₐ is hydrogen, methyl, methoxy or chloro,
R₈''' is methyl, ethyl, 2-hydroxyethyl, 2-hydroxypropyl or 2-carbamoylethyl, R$_{16}''$ is hydrogen, methyl, methoxy, phenoxy, benzyloxy, acetamido, methylsulfonylamino or benzamido, R$_{17}''$ is hydrogen or methyl or R$_{16}''$ and R$_{17}''$ taken together are —CH═CH—CH═CH—, Q$_a'''$ is phenyl, naphthyl or phenyl substituted by chloro or methyl, and A$^\ominus$ is an anion.

26. A compound according to claim 25 wherein

R$_{16}''$ is methoxy, and

R$_{17}''$ is methyl.

27. A compound according to claim 25 wherein

R$_1'''$ is hydrogen,

R$_8'''$ is methyl or ethyl, and

R$_{16}''$ is methoxy.

28. A compound according to claim 13 having the formula

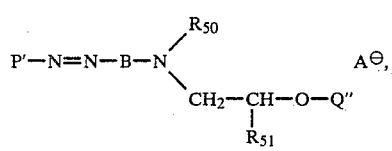

wherein P' is

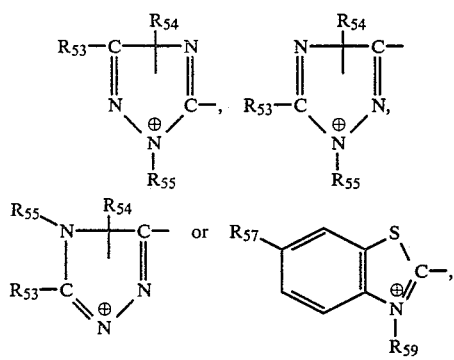

wherein

R$_{53}$ is hydrogen, methyl, phenyl or benzyl, each of R$_{54}$ and R$_{55}$ is independently alkyl of 1 to 4 carbon atoms or alkyl of 1 to 4 carbon atoms monosubstituted by hydroxy or carbamoyl, R$_{57}$ is hydrogen or alkoxy of 1 to 4 carbon atoms, and R$_{59}$ is alkyl of 1 to 4 carbon atoms or alkyl of 1 to 4 carbon atoms monosubstituted by carbamoyl, R$_{50}$ is alkyl of 1 to 4 carbon atoms or alkyl of 1 to 4 carbon atoms monosubstituted by phenyl, R$_{51}$ is hydrogen or alkyl of 1 to 4 carbon atoms, B is

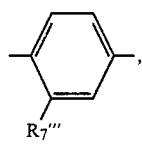

wherein R$_7'''$ is hydrogen or alkyl of 1 to 4 carbon atoms,

Q is

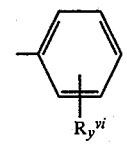

or naphthyl, wherein each

R$^{vi}$ is independently hydroxy, halo, alkoxycarbonyl wherein the alkoxy radical has 1 to 4 carbon atoms, phenoxy, benzoyl, cyclohexyl, alkyl of 1 to 4 carbon atoms, alkyl of 1 to 4 carbon atoms monosubstituted by phenyl or trihalomethyl, and Y is 0, 1, 2, 3, 4 or 5, with the proviso that each R$^{vi}$ is halo when y is 3, 4 or 5, and A$^\ominus$ is an anion.

29. A compound according to claim 28, wherein A$^\ominus$ is chloride, ZnCl$_3^\ominus$, methylsulfate or acetate.

30. A compound according to claim 28 wherein P' is

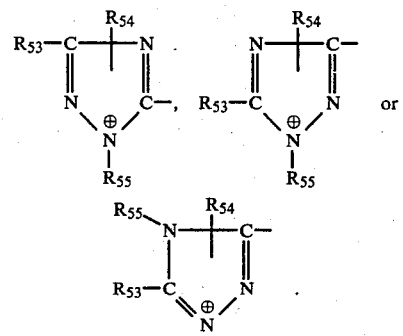

31. A compound according to claim 28 wherein P' is

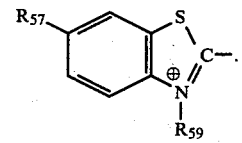

32. A compound according to claim 28 having the formula

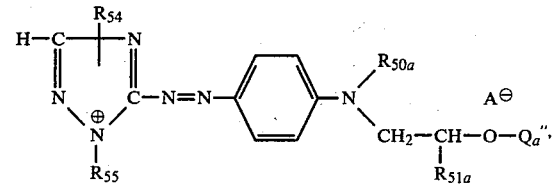

wherein

R$_{50a}$ is alkyl of 1 to 4 carbon atoms,

R$_{51a}$ is hydrogen or methyl, each of R$_{54}$ and R$_{55}$ is independently alkyl of 1 to 4 carbon atoms or alkyl of 1 to 4 carbon atoms monosubstituted by hydroxy or carbamoyl, Q$_{1a}''$ is methylphenyl, dimethylphenyl,

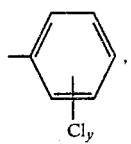

3-hydroxy-4-benzoylphenyl or naphthyl, wherein y is 0, 1, 2, 3, 4 or 5, and $A^{\ominus}$ is an anion.

33. A compound according to claim 32 wherein $A^{\ominus}$ is chloride, $ZnCl_3^{\ominus}$, methylsulfate or acetate.

34. A compound according to claim 33, having the formula

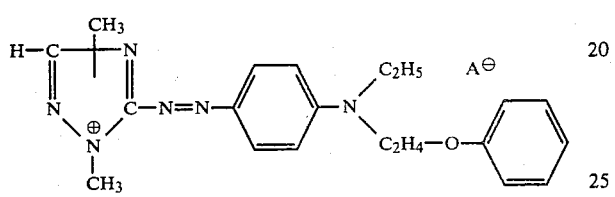

35. A compound according to claim 34 wherein $A^{\ominus}$ is $ZnCl_3^{\ominus}$.

36. A compound according to claim 33 having the formula

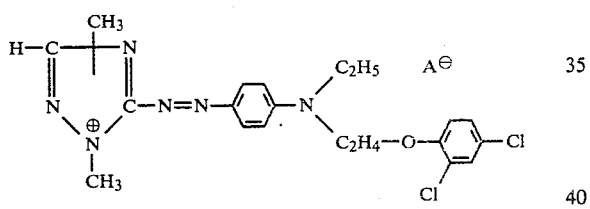

37. A compound according to claim 33 having the formula

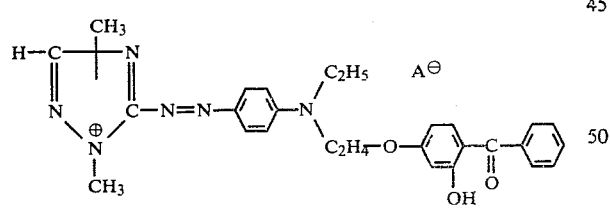

38. A compound according to claim 33 having the formula

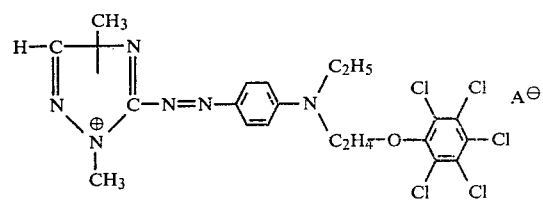

39. A compound according to claim 33 having the formula

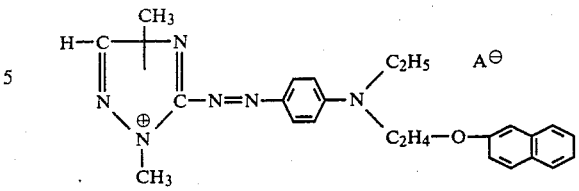

40. A compound according to claim 39 wherein $A^{\ominus}$ is $ZnCl_3^{\ominus}$.

41. A compound according to claim 33 having the formula

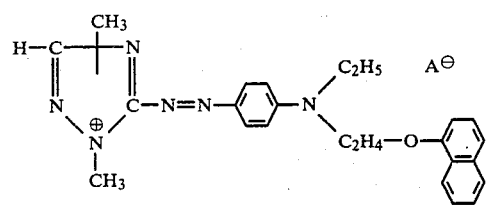

42. A compound according to claim 41 wherein $A^{\ominus}$ is $ZnCl_3^{\ominus}$.

43. A compound according to claim 32 having the formula

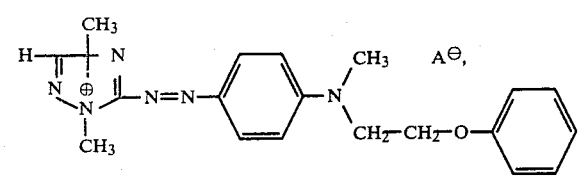

wherein $A^{\ominus}$ is an anion.

44. A compound according to claim 33 having the formula

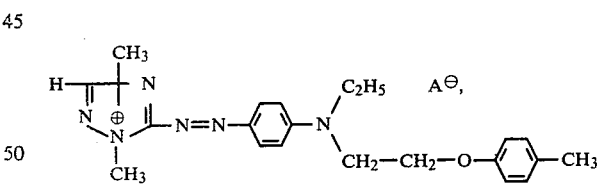

wherein $A^{\ominus}$ is an anion.

45. A compound according to claim 35 having the formula

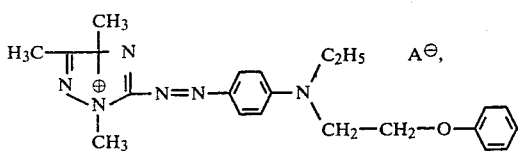

wherein $A^{\ominus}$ is an anion.

46. A compound according to claim 32 having the formula

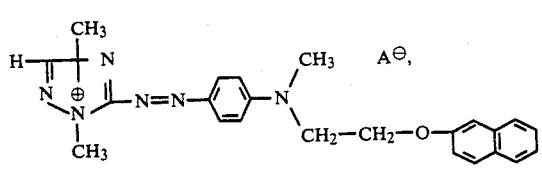
wherein A⊖ is an anion.
47. A compound according to claim 28 having the formula
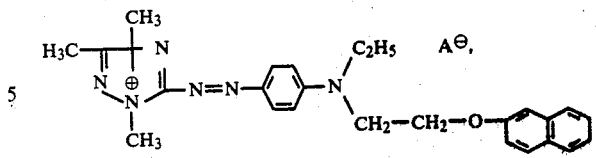
wherein A⊖ is an anion.
48. A compound according to claim 28 having the formula
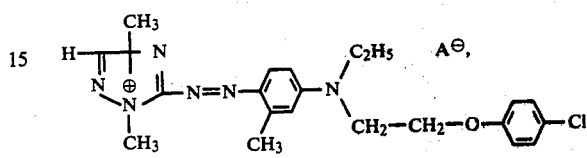
wherein A⊖ is an anion.
49. A compound according to claim 29 having the of formula
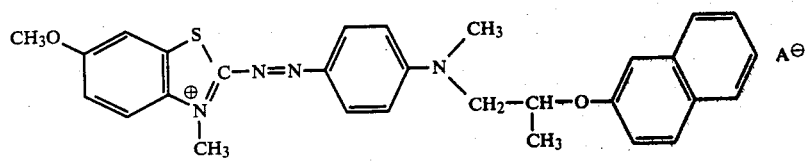
* * * * *